(12) United States Patent
Leopold et al.

(10) Patent No.: US 8,348,994 B2
(45) Date of Patent: Jan. 8, 2013

(54) VASCULAR PROSTHESIS WITH ALTERNATING HELICAL SECTIONS

(75) Inventors: Eric W. Leopold, Redwood City, CA (US); Gerald Ray Martin, Redwood City, CA (US); Michael Hogendijk, Mountain View, CA (US); John Peckham, St. Louis, MO (US); Mary Ann Parker, legal representative, St. Louis, MO (US)

(73) Assignee: NovoStent Corporation, Mountain View, CA (US)

( * ) Notice: Subject to any disclaimer, the term of this patent is extended or adjusted under 35 U.S.C. 154(b) by 1371 days.

(21) Appl. No.: 11/716,472

(22) Filed: Mar. 9, 2007

(65) Prior Publication Data

US 2008/0221663 A1  Sep. 11, 2008

(51) Int. Cl.
*A61F 2/06* (2006.01)
(52) U.S. Cl. ...................................... 623/1.22; 623/1.16
(58) Field of Classification Search .................. 623/1.22, 623/1.16
See application file for complete search history.

(56) References Cited

U.S. PATENT DOCUMENTS

| 4,553,545 | A | | 11/1985 | Maass et al. | |
|---|---|---|---|---|---|
| 4,760,849 | A | | 8/1988 | Kropf | |
| 4,800,882 | A | * | 1/1989 | Gianturco | 606/194 |
| 4,969,458 | A | * | 11/1990 | Wiktor | 623/1.11 |
| 5,342,387 | A | * | 8/1994 | Summers | 606/198 |
| 5,603,722 | A | | 2/1997 | Phan et al. | |
| 5,607,445 | A | | 3/1997 | Summers | |
| 5,632,771 | A | | 5/1997 | Boatman et al. | |
| 5,707,387 | A | * | 1/1998 | Wijay | 623/1.2 |
| 5,772,668 | A | | 6/1998 | Summers et al. | |
| 5,797,952 | A | | 8/1998 | Klein | |
| 5,824,052 | A | | 10/1998 | Khosravi et al. | |
| 5,824,053 | A | | 10/1998 | Khosravi et al. | |
| 6,080,191 | A | | 6/2000 | Summers | |
| 6,273,908 | B1 | | 8/2001 | Ndondo-Lay | |
| 6,409,752 | B1 | | 6/2002 | Boatman et al. | |
| 6,425,915 | B1 | | 7/2002 | Khosravi et al. | |
| 6,464,720 | B2 | | 10/2002 | Boatman et al. | |
| 6,508,834 | B1 | * | 1/2003 | Pinchasik et al. | 623/1.16 |
| 6,514,285 | B1 | | 2/2003 | Pinchasik | |
| 6,562,064 | B1 | | 5/2003 | deBeer | |
| 6,572,648 | B1 | | 6/2003 | Klumb et al. | |
| 6,607,551 | B1 | | 8/2003 | Sullivan et al. | |
| 6,645,237 | B2 | | 11/2003 | Klumb et al. | |

(Continued)

FOREIGN PATENT DOCUMENTS

WO   WO 00/62711   10/2000

(Continued)

OTHER PUBLICATIONS

Written Opinion on related application PCT/US08/056083 dated Aug. 22, 2005.*

(Continued)

*Primary Examiner* — Paul Prebilic
(74) *Attorney, Agent, or Firm* — James F. Hann; Haynes Beffel & Wolfeld LLP

(57) ABSTRACT

An implantable vascular prosthesis is provided for use in a wide range of applications wherein at least first and second helical sections having alternating directions of rotation are coupled to one another. The prosthesis is configured to conform to a vessel wall without substantially remodeling the vessel, and permits accurate deployment in a vessel without shifting or foreshortening.

20 Claims, 18 Drawing Sheets

U.S. PATENT DOCUMENTS

| | | |
|---|---|---|
| 2002/0004679 A1 | 1/2002 | Eury et al. |
| 2002/0151956 A1 | 10/2002 | Chobotov et al. |
| 2004/0122504 A1 | 6/2004 | Hogendijk |
| 2004/0186556 A1 | 9/2004 | Hogendijk |
| 2005/0165469 A1 | 7/2005 | Hogendijk |
| 2006/0079955 A1 | 4/2006 | Brown |
| 2006/0136033 A1 | 6/2006 | Hermann et al. |
| 2006/0136035 A1 | 6/2006 | Hermann et al. |
| 2007/0048350 A1 | 3/2007 | Falotico et al. |
| 2007/0185560 A1* | 8/2007 | Roeder et al. ............... 623/1.15 |
| 2007/0208416 A1 | 9/2007 | Burpee et al. |
| 2008/0221658 A1* | 9/2008 | Martin et al. ............... 623/1.12 |
| 2008/0221665 A1* | 9/2008 | Peckham et al. ............ 623/1.22 |

FOREIGN PATENT DOCUMENTS

WO     WO-2006/108010 A2 * 10/2006

OTHER PUBLICATIONS

International Search Report dated Aug. 22, 2008 from corresponding International App. No. PCT/US 08/56083.

Extended EP Search Report dated Jul. 30, 2010, from corresponding EP Application No. 08731571.9; 7 pages.

* cited by examiner

VASCULAR PROSTHESIS WITH ALTERNATING HELICAL SECTIONS

FIELD OF THE INVENTION

The present invention relates to an implantable vascular prosthesis configured for use in a wide range of applications, and more specifically, to a prosthesis having an alternating helical section.

BACKGROUND OF THE INVENTION

Today there are a wide range of intravascular prostheses on the market for use in the treatment of aneurysms, stenoses, and other vascular irregularities. Balloon expandable and self-expanding stents are well known for restoring patency in a stenosed vessel, e.g., after an angioplasty procedure, and the use of coils and stents are known techniques for treating aneurysms.

Previously-known self-expanding stents generally are retained in a contracted delivery configuration using an outer sheath, then self-expand when the sheath is retracted. Such stents commonly have several drawbacks, for example, the stents may experience large length changes during expansion (referred to as "foreshortening" or "jumping") and may shift within the vessel prior to engaging the vessel wall, resulting in improper placement. Another disadvantage is that after the stent is deployed it can experience longitudinal movement within the vessel (also referred to as "migration"), which can be attributed to repetitive longitudinal loading and unloading of the stent.

Additionally, repetitive loading and unloading of a stent have also been known to cause fatigue induced strut failure, which may contribute to restenosis and subsequent vessel narrowing and/or occlusion. Additionally, many self-expanding stents have relatively large delivery profiles because the configuration of their struts limits further compression of the stent. Accordingly, such stents may not be suitable for use in smaller vessels, such as cerebral vessels and coronary arteries.

For example, PCT Publication WO 00/62711 to Rivelli describes a stent comprising a helical mesh coil having a plurality of turns and including a lattice having a multiplicity of pores. The lattice is tapered along its length. In operation, the plurality of turns are wound into a reduced diameter helical shape, and then constrained within a delivery sheath. The delivery sheath is retracted to expose the distal portion of the stent and anchor the distal end of the stent. As the delivery sheath is further retracted, subsequent individual turns of the stent unwind to conform to the diameter of the vessel wall.

The stent described in the foregoing publication has several drawbacks. For example, due to friction between the turns and the sheath, the individual turns of the stent may "bunch up," or overlap with one another, when the delivery sheath is retracted. In addition, once the sheath is fully retracted, the turns may shift within the vessel prior to engaging the vessel wall, resulting in improper placement of the stent. Moreover, because the distal portion of the stent may provide insufficient engagement with the vessel wall during subsequent retraction of the remainder of the sheath, ambiguity concerning accuracy of the stent placement may arise.

In another example, U.S. Pat. No. 5,603,722 to Phan et al. describes a stent formed of expandable strip-like segments. The strip-like segments are joined along side regions in a ladder-like fashion along offsetting side regions. A shortcoming of such a stent is that the junctions between adjacent segments are not provided with a means of addressing longitudinal loading. As a result, such a stent is susceptible to strut fracture.

In another example, U.S. Pat. No. 5,607,445 to Summers describes a balloon expandable stent. In one embodiment, the stent is constructed from a single wire that is configured so that each half of the wire is zig-zagged and curved to generally form a half-cylinder. The zig-zags of each half-cylinder are intermeshed so that they combine to form a cylindrical stent. The stent described in the foregoing publication has several drawbacks. The stent does not allow for longitudinal loading. As a result, applying a longitudinal load will cause the bends to move radially inward which will bias them into the vessel flow. Additionally, the stent design may be susceptible to fracture with repetitive loading and unloading.

In yet another example, U.S. Pat. No. 5,707,387 to Wijay describes a stent constructed from a plurality of bands, where each band is composed of a solid wire-like material formed into a closed, substantially rectangular shape. Each band is circumferentially offset from the adjacent band and adjacent bands are connected by one or more cross-tie members. This stent also has several drawbacks. The rectangular cell design does not allow for longitudinal loading because the cells are not flexible. Therefore, under a longitudinal load the apex will move out of plane and will be biased into the vessel (i.e., into the vessel flow). Secondly the stent may be susceptible to fracture with repetitive loading and unloading because of the rigid cells.

When utilizing stents in interventional procedures, it may be advantageous to deliver therapeutic agents to a vessel wall via the surface of the stent. Drug eluting stents have many advantages, such as controlled delivery of therapeutic agents over an extended period of time without the need for intervention, and reduced rates of restenosis after angioplasty procedures. Typically, the drug is disposed in the matrix of a bioabsorbable polymer coated on an exterior surface of the struts of the stents, and then gradually released into a vessel wall. The quantity of the therapeutic agent provided by the stent generally is limited by the surface area of the struts. Increasing the surface area of the struts may enhance drug delivery capability, but may compromise the overall delivery profile of the stent. There therefore exists a need for a prosthesis having a reduced delivery profile and enhanced drug delivery capabilities. This would be especially beneficial if other attributes such as radial strength and flexibility are not compromised.

In view of the drawbacks of previously known devices, it would be desirable to provide apparatus and methods for an implantable vascular prosthesis comprising a plurality of helical portions joined together, wherein the prosthesis is configured to be used in a wide range of applications including maintaining patency in a vessel and delivering drugs to a vessel.

It also would be desirable to provide apparatus and methods for a vascular prosthesis that is flexible enough to conform to a natural shape of a vessel without substantially remodeling the vessel.

It further would be desirable to provide apparatus and methods for a vascular prosthesis having one or more radially expanding anchors that allow for additional control over the deployment of the vascular prosthesis at a desired location within a vessel.

It still further would be desirable to provide apparatus and methods for a vascular prosthesis that has a surface area that may be selected to facilitate in-vivo delivery of therapeutic agents without adversely impacting the mechanical properties (e.g., radial strength, flexibility, etc.) of the prosthesis.

It additionally would be desirable to provide apparatus and methods for a vascular prosthesis that has a strut configuration that allows for repetitive longitudinal loading and unloading of the prosthesis.

It further would be desirable to provide apparatus and methods for a vascular prosthesis that has a structure having the ability to absorb or distribute loads.

It yet further would be desirable to provide apparatus and methods for a vascular prosthesis that has a small delivery configuration to allow the prosthesis to be used in smaller vessels.

SUMMARY OF THE INVENTION

In view of the foregoing, it is an object of the present invention to provide apparatus and methods for an implantable vascular prosthesis comprising a plurality of helical stent portions having alternating directions of rotation joined together, wherein the prosthesis is configured to be used in a wide range of applications including, but not limited to, maintaining patency in a vessel and delivering drugs to a vessel.

It is a further object of the present invention to provide apparatus and methods for a vascular prosthesis that is flexible enough to conform to a natural shape of a vessel without substantially remodeling the vessel.

It is another object of the present invention to provide apparatus and methods for a vascular prosthesis having at least one alternating helical section that allows for controlled deployment of the vascular prosthesis at a desired location within a vessel.

It is another object of the present invention to provide apparatus and methods for a vascular prosthesis having a strut configuration that dampens the stresses associated with repetitive longitudinal loading and unloading, torsional loads, buckling and bending.

It is another object of the present invention to provide apparatus and methods for a vascular prosthesis having independent cells that absorb and/or distribute loads applied to the prosthesis.

It is a further object of the present invention to provide apparatus and methods for a vascular prosthesis that has a surface area that facilitates in-vivo delivery of therapeutic agents.

It is a further object of the present invention to provide apparatus and methods for a vascular prosthesis that has a small delivery configuration to allow the prosthesis to be used in smaller vessels.

These and other objects of the present invention are accomplished by providing a vascular prosthesis comprising a plurality of helical portions having alternating directions of rotation that are joined together. The prosthesis is configured to engage a vessel wall and adapt to a natural curvature of the vessel. The vascular prosthesis may be used in a wide range of applications.

In a preferred embodiment, the vascular prosthesis comprises a shape memory material, such as Nitinol, and includes an alternating helical section. As used in this specification, an "alternating helical section" is formed of two or more helical portions that are joined together and have at least one change in direction of rotation of the helices.

Prostheses of the present invention are delivered to a target vessel in a contracted state, constrained within an outer sheath, in which radially inwardly directed compressive forces are applied by the outer sheath to the anchor section(s). In the contracted state, the helical section is wound down to a reduced diameter configuration, so that adjacent turns preferably partially overlap. As an alternative, the helical section may be configured so that there is no overlap if desired. As a still further alternative, the helical section may be compressed radially to a reduced diameter configuration in addition to or in lieu of winding.

In a preferred method of operation of a prosthesis the alternating helical section is provided in its contracted state within an outer sheath and the prosthesis is fluoroscopically advanced into a selected vessel using techniques that are known in the art. The alternating helical section then is positioned adjacent a target region of a vessel, such as a stenosed region. The outer sheath then is retracted proximally to cause the first helical portion(s) of the alternating helical section to self-deploy and engage the vessel wall at the target region. Advantageously, by overlapping portions of the alternating helical section, the alternating helical section will expand in a controlled manner. This technique ensures that the prosthesis will not shift within the vessel during deployment.

The vascular prosthesis of the present invention is flexible enough to conform to the shape of a vessel without substantially remodeling the vessel.

Additionally, the mesh configuration of the alternating helical section preferably conforms to the vasculature of the target region since each of the plurality of turns is free to assume a curved configuration substantially independently of one another. Also, because the alternating helical section of the vascular prosthesis has a ribbon-like helical structure, it may be rolled down to a contracted state with a more accurate reduced delivery profile, compared to slotted-tube stents. This feature makes the stent of the present invention especially useful for treating defects in smaller vessels, such as cerebral arteries.

In accordance with another aspect of the present invention, the plurality of turns of the alternating helical section may comprise a substantially increased surface area relative to conventional stents that have a plurality of interconnected struts. The increased surface area of the turns is particularly advantageous for localized drug delivery. The turns may be coated with a drug-laden polymer coating or, alternatively, one or more dimples or through-holes may be disposed in a lateral surface of the turns to elute drugs over an extended period of time.

Methods of using the vascular prosthesis of the present invention, for example, in the treatment of the peripheral vasculature, also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The vascular prosthesis, according to the present invention, has an alternating helix configuration that provides a more accurate reduced delivery profile than previously known devices. Additionally, the prosthesis is configured to conform to a vessel wall without substantially remodeling the vessel, to provide improved compression resistance, deployment accuracy, migration resistance and load dampening characteristics.

Figure 1:
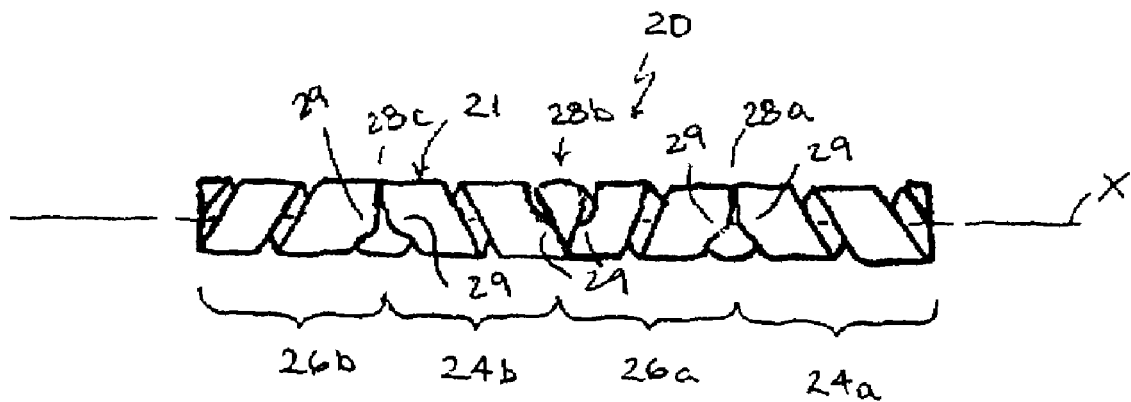
FIG. 1 is a schematic representation of a vascular prosthesis of the present invention in a deployed state.
Figure 2:
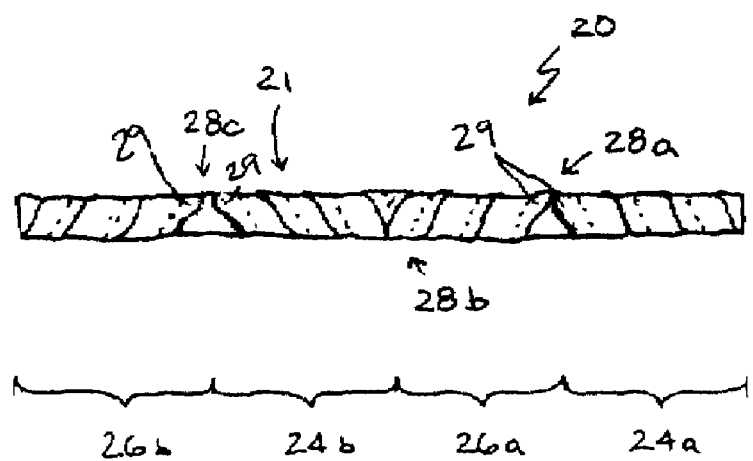
FIG. 2 is a schematic representation of the vascular prosthesis of the present invention in a contracted state.

Referring now to FIGS. 1 and 2, a schematic representation of a vascular prosthesis constructed in accordance with principles of the present invention is described. Vascular prosthesis ("stent") 20 illustratively comprises alternating helical section 21 capable of assuming contracted and deployed states. In FIG. 1, alternating helical section 21 is depicted in the deployed state.

Alternating helical section 21 is constructed from two or more helical portions having at least one change in the direction of rotation of the helices, and being joined at apex portions where the directions of rotation of adjacent helices change. In particular, first (i.e., proximal-most) helical portion 24a has a generally clockwise rotation about longitudinal axis X of prosthesis 20. Helical portion 26a adjoins the distal end of helical portion 24a at apex 28a and has a generally counter-clockwise rotation about longitudinal axis X. Helical portion 24b adjoins the distal end of helical portion 26a at apex 28b, and in turn is coupled to the proximal end of helical portion 26b at apex 28c. As a result of the alternating direction of rotation of the adjoining helical portions 24a, 26a, 24b and 26b of vascular prosthesis 20 includes three apices 28a, 28b and 28c that are oriented such that they point in alternating directions about the circumference of vascular prosthesis 20, generally in a plane that is normal to longitudinal axis X of vascular prosthesis 20. Preferably, each helical portion includes at least one full helical turn between adjacent apices. However, each helical portion may include more or less turns between adjacent apices, for example a helical portion may include 0.5-2.0 helical turns between adjacent apices.

The terminal ends of the alternating helical section may have any desired configuration. For example, as shown in FIG. 1, the terminal ends, or tails, of alternating helical section 21 cut along a plane that is perpendicular to the longitudinal axis of vascular prosthesis 20. Alternatively, the terminal ends may be cut along any plane, such as for example parallel to the longitudinal axis. The terminal ends may end in a pointed or rounded tip or they may be truncated. As a further alternative, the width of the ribbon or mesh that forms the terminal helical portions may be varied. For example, the width of the ribbon of the terminal helical portion may taper so that it has the largest width adjacent the nearest apex and the smallest width near the terminal end. These features may be selected to provide a desired transitional flexibility at the ends of the alternating helical portion. That transitional flexibility may be used to assure that the curvature of a vessel remains smooth near the end of the stent.

A significant advantage of alternating helical section 21 as compared to other vascular prosthesis structures, is that the apices of the alternating helical section provide additional anchoring force at discrete locations along the length of the alternating helical section. That anchoring force may be used to increase the radial force applied by the vascular prosthesis to a vessel wall as well as providing additional migration resistance. That anchoring force may be increased if desired by flaring out the ends and/or apices of the alternating helical section. Those portions may be flared outward by applying expansion and heat treatment so that those portions have a larger expanded diameter than the remainder of alternating helical section 21. Additionally, the alternating helical configuration also allows the wall thickness of the device to be reduced because the design provides increased radial strength.

Flanges 29 are included at each apex 28. Each flange 29 is configured so that a portion of a corresponding apex 28 may overlap a portion of flange 29 in both the contracted and deployed states. Overlap of apex 28 and a corresponding flange 29 provides reinforcement at apex 28 to increase the radial strength (i.e., resistance to radial compression) of the alternating helical section at the apex. Additionally, the flange provides improved metal coverage because it may be used to reduce or eliminate a gap between an apex and the corresponding flange when the stent is in a deployed configuration. The flange allows the stent to be configured so that there is overlap at a small diameter and a controlled gap at a large diameter without requiring side-to-side overlap throughout the alternating helical section.

In the illustrated embodiment, each helical portion 24, 26 includes flange 29 adjacent apex 28, which is a widening of the adjacent helical portions 24, 26 so that the gap therebetween is reduced. For example, in an embodiment apices 28a and 28c remain radially inward of flanges 29 while apex 28b remains radially outward of flanges 29 throughout use. It should be appreciated however that the stent may be configured so that at the largest expanded diameter there is a gap between an apex and the corresponding flange.

Alternating helical section 21 preferably is formed from a solid tubular member comprised of a shape memory material, such as nickel-titanium alloy (commonly known in the art as Nitinol). However, it should be appreciated that alternating helical section 21 may be constructed from any suitable material recognized in the art. The solid tubular member then is laser cut, using techniques that are known in the art, to define a specific pattern or geometry in the deployed configuration. Preferably, alternating helical section 21 is cut from the tube so that helical portions 24a, 26a, 24b, 26b are integrally formed as a single monolithic body. However, it should be appreciated that separate helical portions may be mechanically coupled, such as by welding, soldering or installing mechanical fasteners to construct alternating helical section 21. An appropriate expansion and heat treatment then may be applied to alternating helical section 21 of vascular prosthesis 20 so that the device may be configured to self-deploy from a contracted, delivery configuration to the deployed configuration.

Referring now to FIG. 2, vascular prosthesis 20 is shown in the contracted, delivery configuration, wherein alternating helical section 21 is in the contracted, reduced diameter state. Alternating helical section 21, however, is placed in the contracted state by winding helical portions 24, 26 about longitudinal axis X. In FIG. 2, apices 28a and 28c may be temporarily engaged to the inner shaft of a delivery catheter, and the shaft is rotated while apex 28b and the distal and proximal ends of alternating helical section 21 are held stationary.

Consequently, apices 28a and 28c are tightly wound onto the shaft of the delivery catheter and the remainder of each helical portion 24, 26 is wound against the shaft so that each turn of each portion 24, 26 overlaps an adjacent turn. For example, in some embodiments, approximately ⅔ of a layer is overlapped by the next layer. As a result, apex 28b and the distal and proximal ends of alternating helical section 21 are located furthest radially outward on the rolled alternating helical section 21. The overlap of the turns of helical portions 24, 26 are indicated by dashed lines in FIG. 2. The overlapping turns and flanges 29 of alternating helical section 21 thus secure apices 28a and 28c when vascular prosthesis 20 is disposed within a delivery system.

Figure 3:
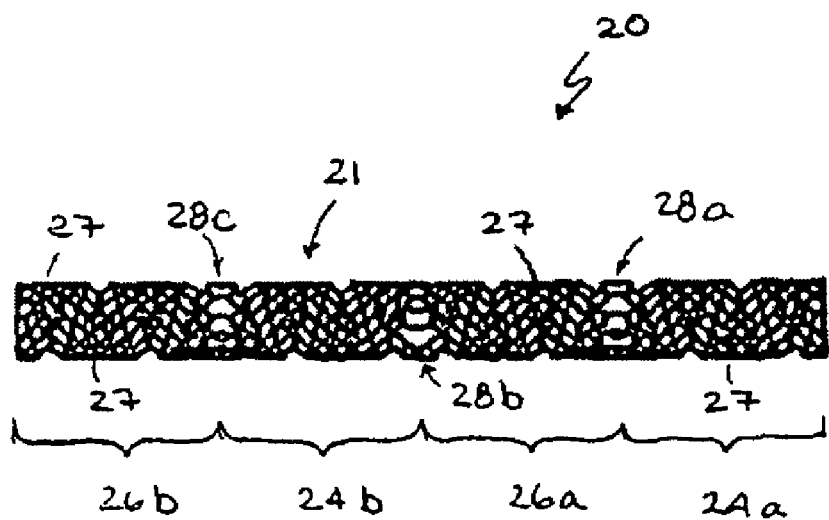
FIG. 3 is a side view of a vascular prosthesis of the present invention.
Figure 4:
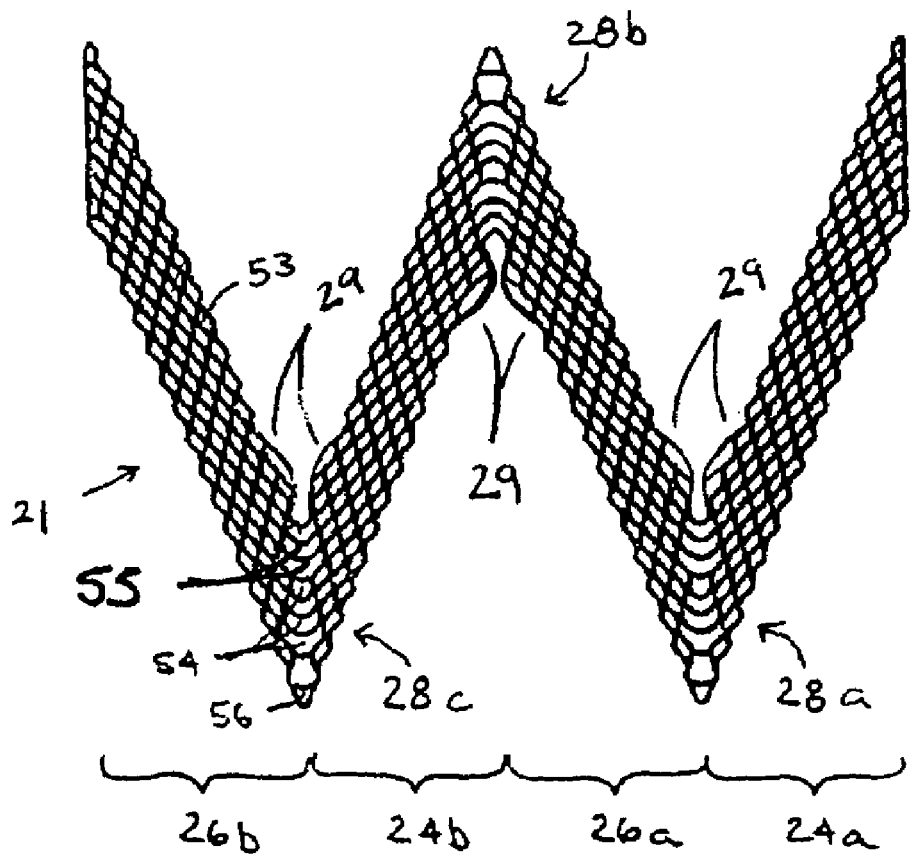
FIG. 4 is a schematic representation of the vascular prosthesis of FIG. 3 shown in a flattened configuration.

Referring now to FIGS. 3 and 4, an embodiment of vascular prosthesis 20, constructed in accordance with principles of the present invention, is described. It should be appreciated that FIG. 4 is a schematic view of vascular prosthesis 20 as it would appear if it were flattened. The components of vascular prosthesis 20 are identical to those depicted in FIGS. 1 and 2 and identical reference numbers are employed in the following description.

Alternating helical section 21 preferably comprises a helical mesh configuration including two or more helical portions 27. Helical portions 27 may include multiplicity of openings 53, 54, 56 of different shapes and sizes. The shape, size and orientation of any particular opening is selected to provide a desired response to longitudinal loads and also may be dependent upon the location of the openings within the mesh structure. The shape, size and orientation of the opening may also be selected to provide desired deployment, unwrapping, radial force and surface area coverage characteristics.

As shown in FIG. 4, alternating helical section 21 includes diamond-shaped openings 53 of generally equal size through the majority of each helical portion 24, 26.

A wide variety of openings may be employed at apices 28a, 28b and 28c, where the helical portions adjoin adjacent helical portions and flanges 29. The openings may have any shape and/or size desired. Some designs include diamond, polygon, circles, ellipses, elongated diamonds, etc. In addition, the openings of apices 28 and flanges 29 need not be symmetric with respect to a centerline of apex 28. It should be appreciated that the size, shape and orientation of any of the openings may be selected so that in the deployed state some struts may bow radially outward or inward so that they interlock with adjacent overlapping openings.

In FIG. 4, each apex includes plurality of openings 54 and one tip opening 56 that forms a tip of the respective apex, which may be triangular as shown. Openings 54 are defined by struts 55 that extend between adjacent helical portions 24, 26.

Figure 5:
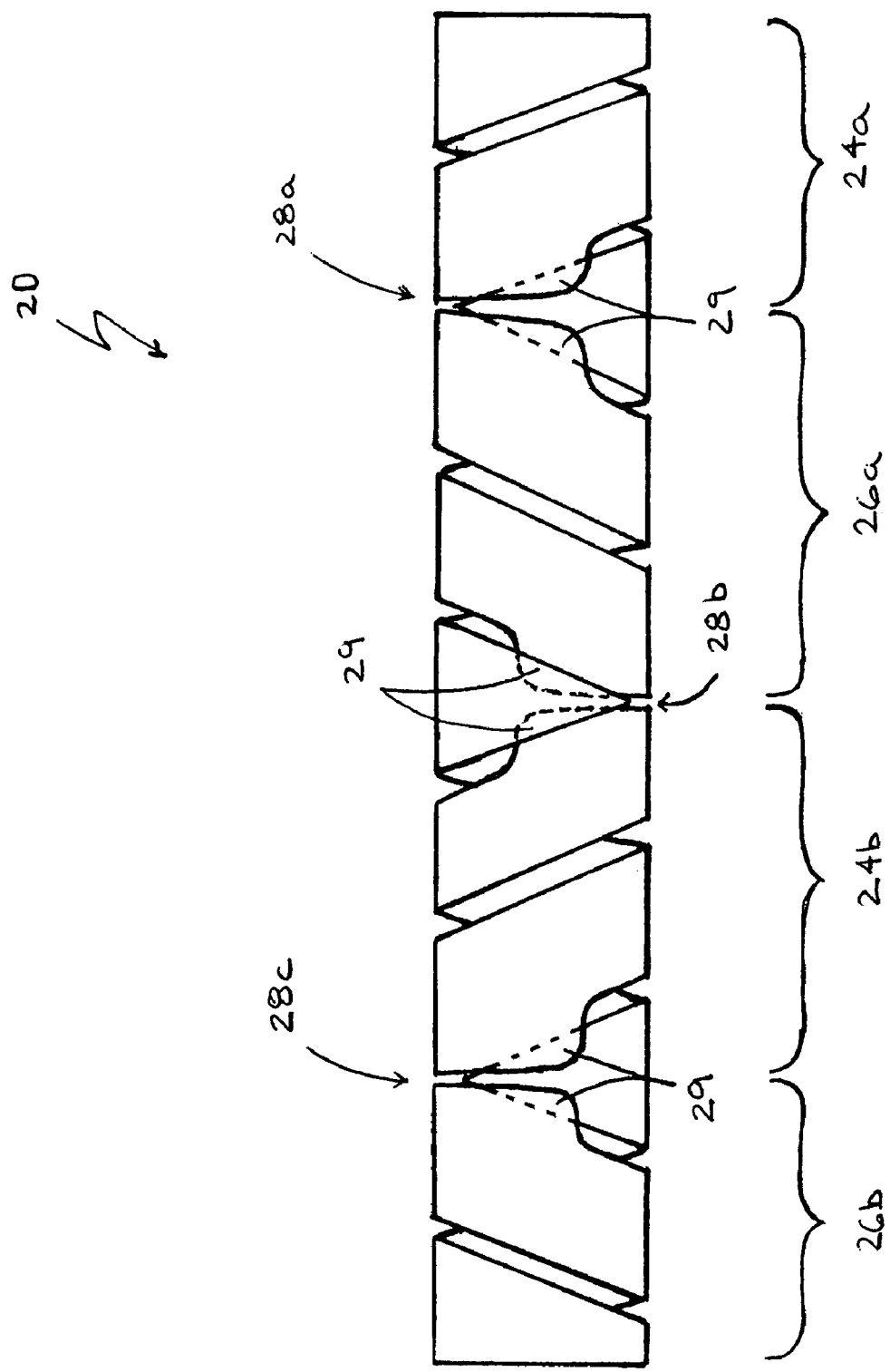
FIG. 5 is an enlarged side view of a vascular prosthesis of the present invention in a deployed state.

Referring to FIG. 5, the interaction between apices 28 and flanges 29 will be described in greater detail. Flanges 29 are formed by widened helical portions 24, 26 adjacent to apices 28. In particular, helical portions 24, 26 are widened so that the gap between two adjacent portions 24, 26 is reduced. As shown by dashed lines, in the deployed state a tip portion of each apex 28 overlaps flange 29 in the deployed state. In the present embodiment, it is preferred to maintain the two lateral apices, 28a, 28c, radially inward and flanges 29 assure that they remain in that position. It will be appreciated that flanges 29 of adjacent helical portions 24, 26 may be joined if desired to provide additional overlap between flange 29 and apex 28.

Figure 7:
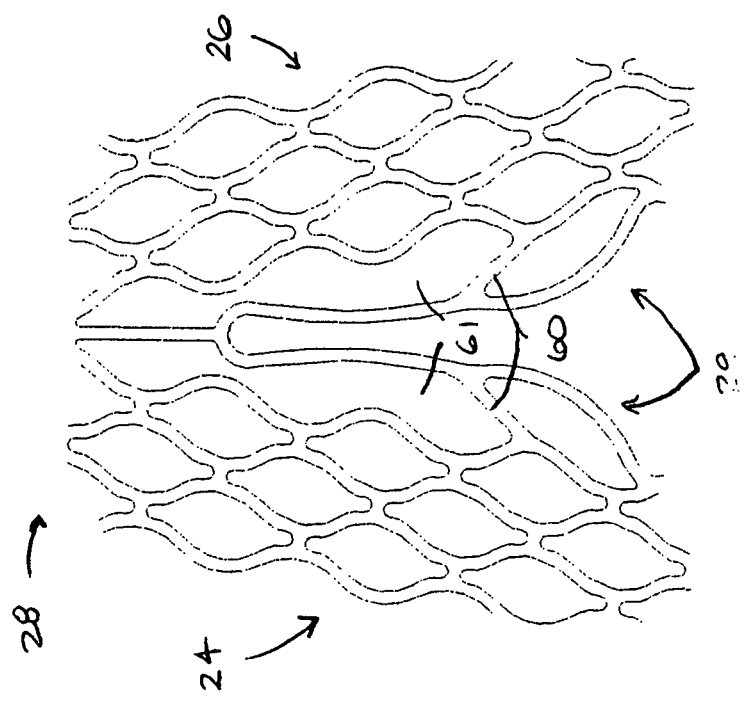
FIG. 7 is an enlarged side view of a portion of an embodiment of a vascular prosthesis of the present invention.
Figure 6:
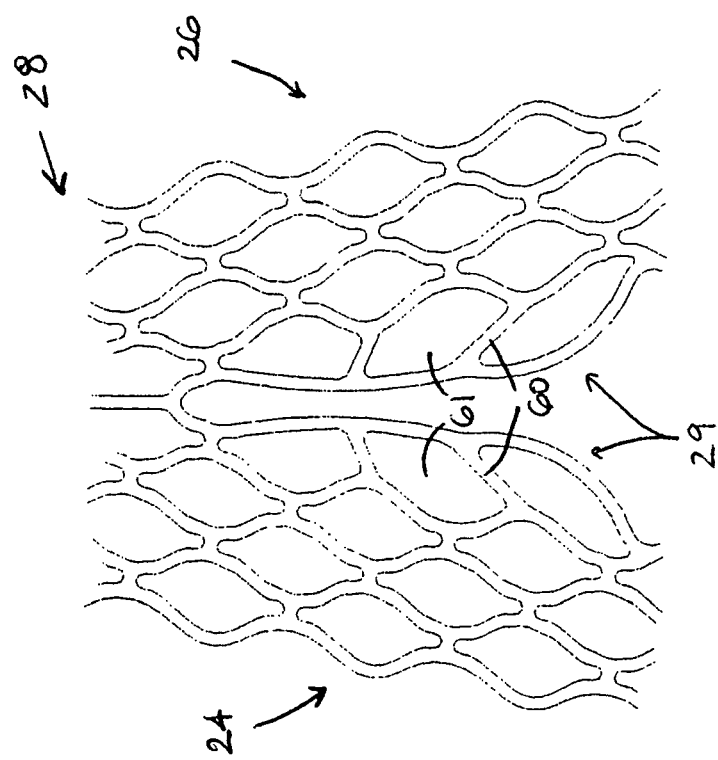
FIG. 6 is an enlarged side view of a portion of an embodiment of a vascular prosthesis of the present invention.
Figure 9:
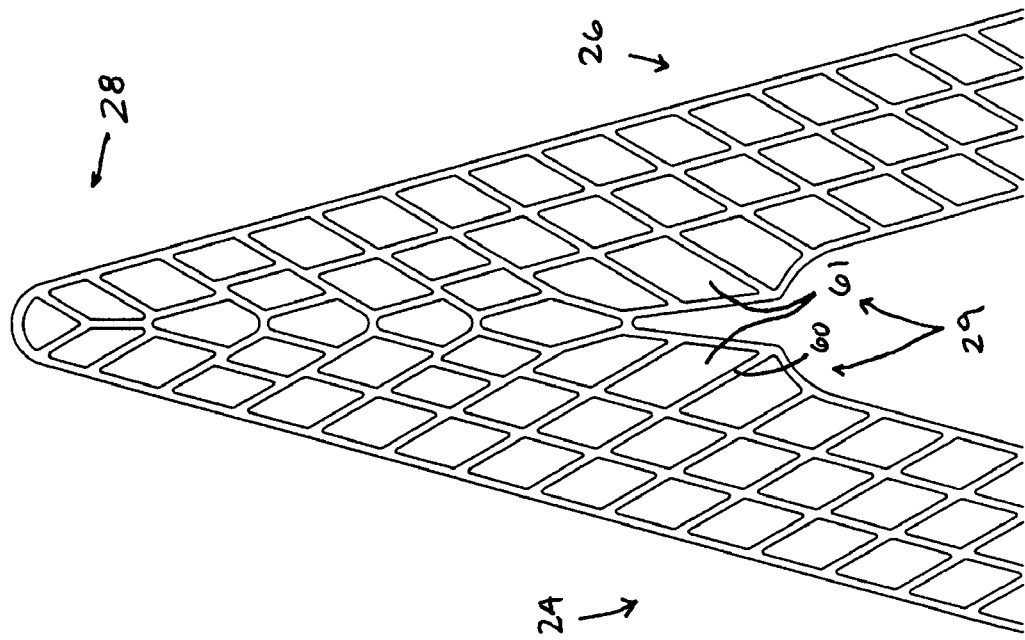
FIG. 9 is an enlarged side view of a portion of an embodiment of a vascular prosthesis of the present invention.
Figure 8:
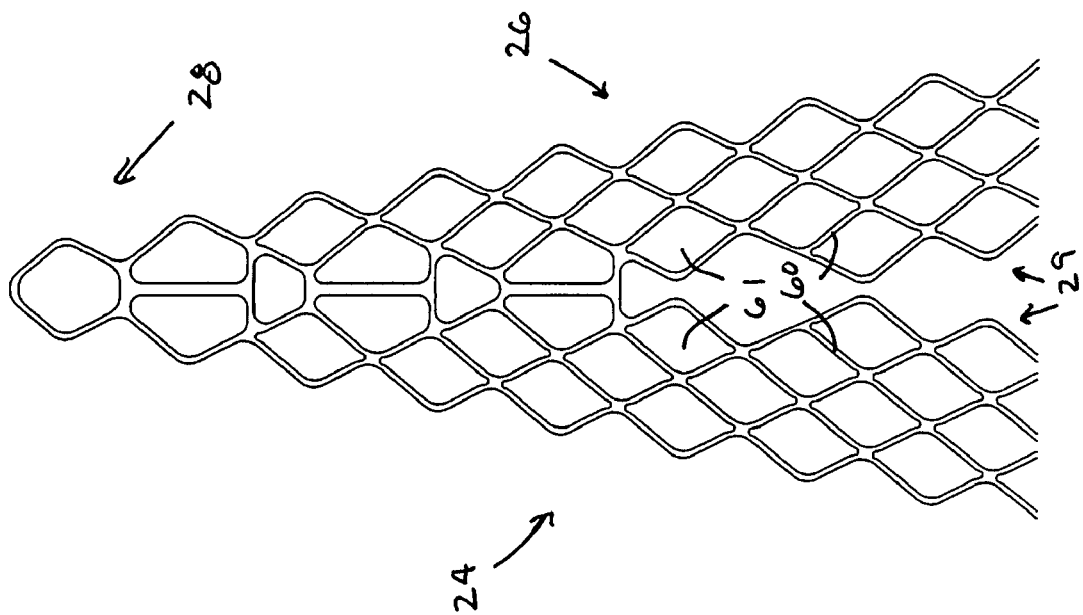
FIG. 8 is an enlarged side view of a portion of an embodiment of a vascular prosthesis of the present invention.
Figure 10:
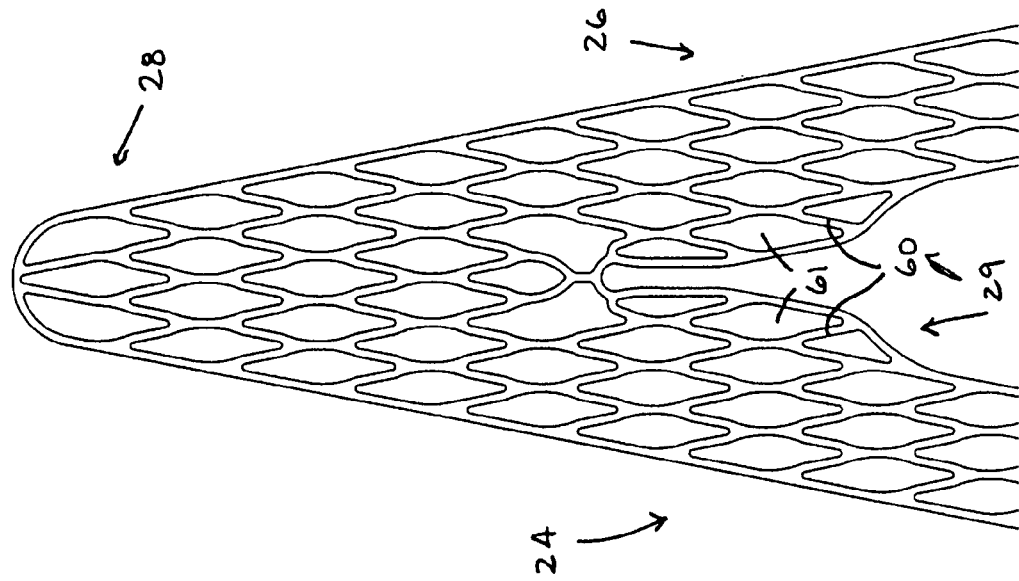
FIG. 10 is an enlarged side view of a portion of an embodiment of a vascular prosthesis of the present invention.
Figure 11:
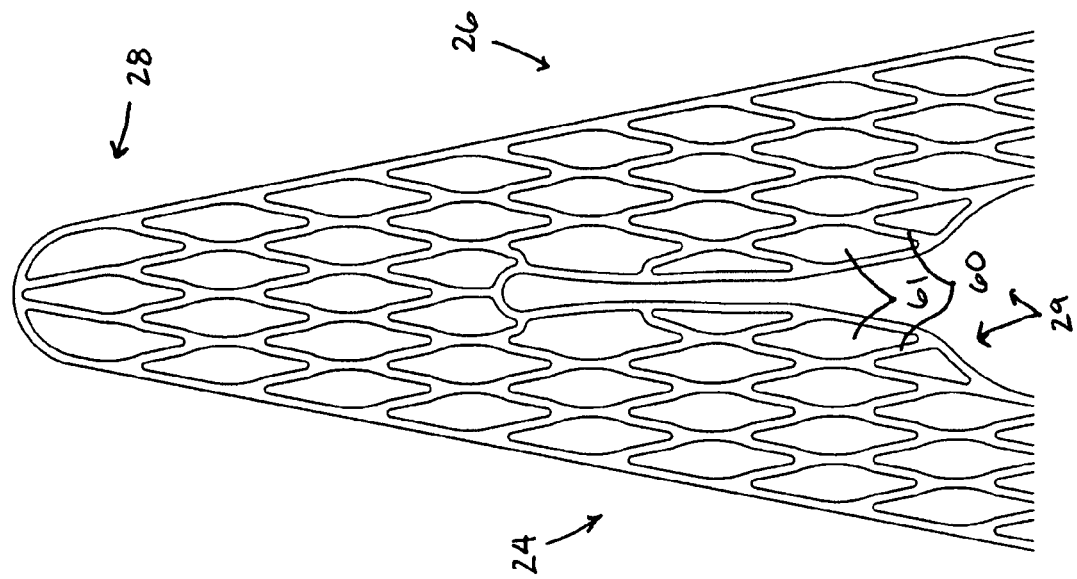
FIG. 11 is an enlarged side view of a portion of an embodiment of a vascular prosthesis of the present invention.
Figure 13:
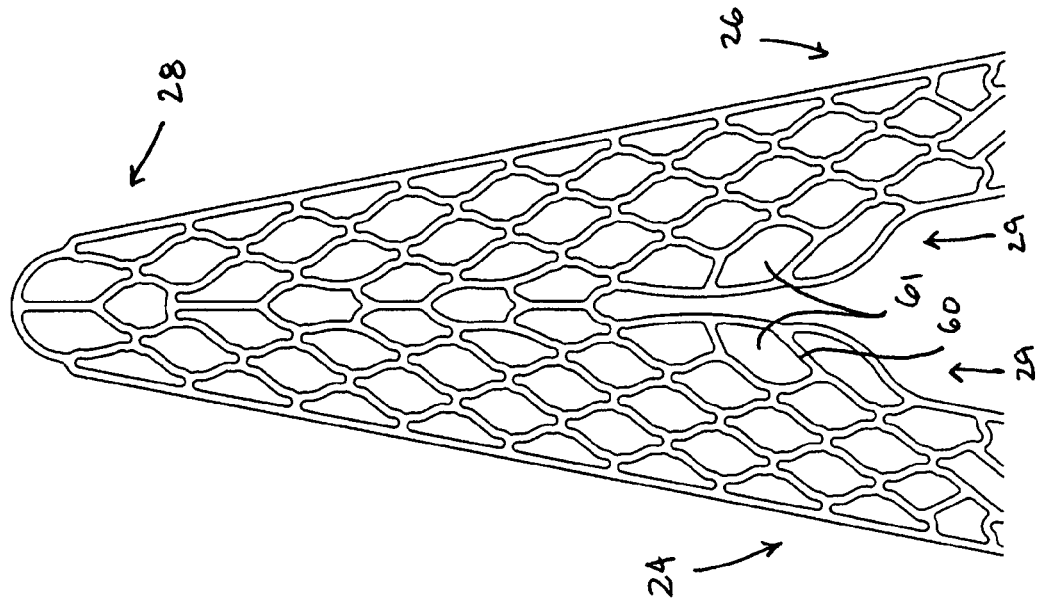
FIG. 13 is an enlarged side view of a portion of an embodiment of a vascular prosthesis of the present invention.
Figure 12:
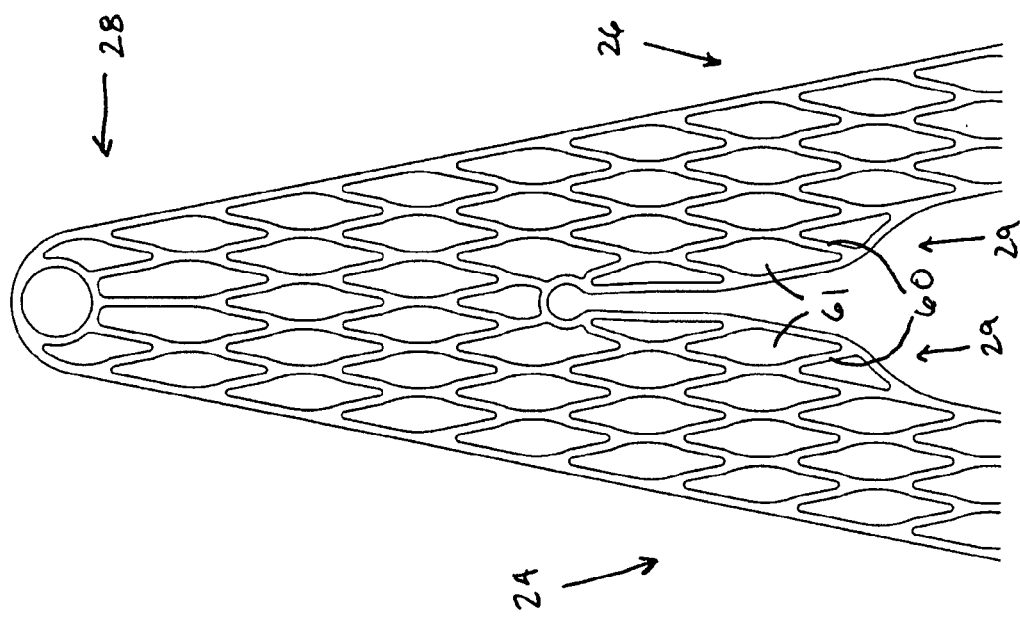
FIG. 12 is an enlarged side view of a portion of an embodiment of a vascular prosthesis of the present invention.
Figure 15:
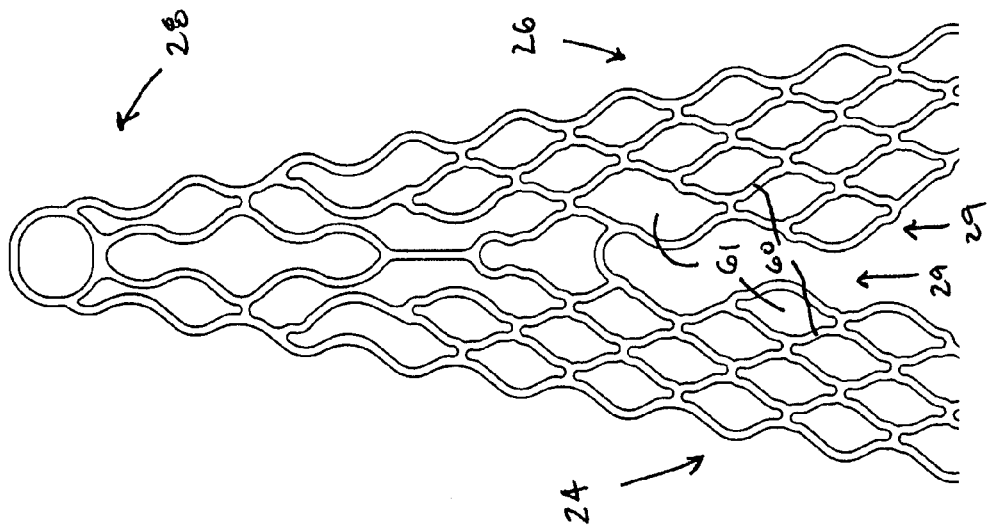
FIG. 15 is an enlarged side view of a portion of an embodiment of a vascular prosthesis of the present invention.
Figure 14:
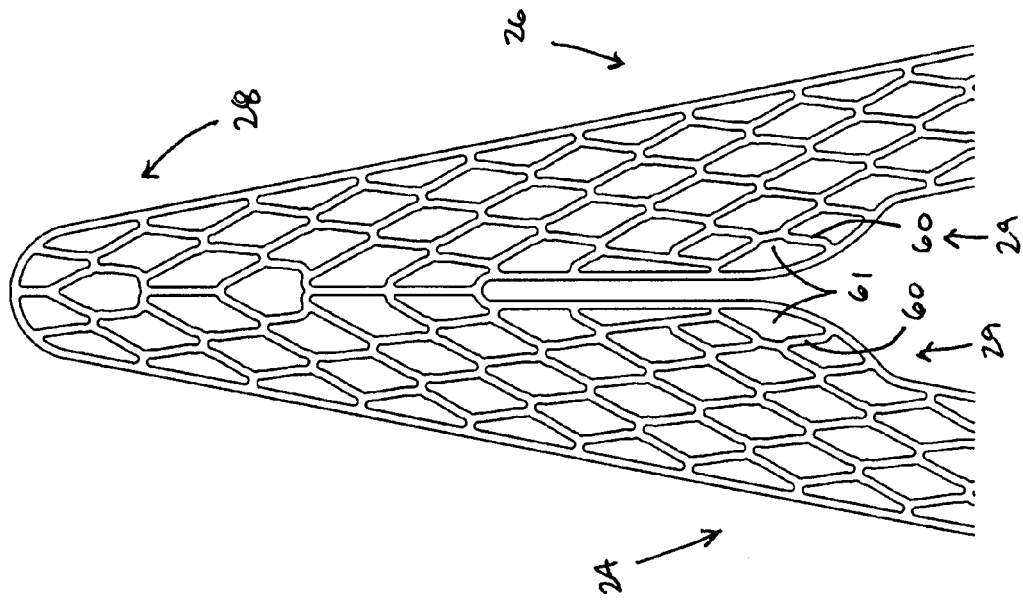
FIG. 14 is an enlarged side view of a portion of an embodiment of a vascular prosthesis of the present invention.

Referring to FIGS. 6-15, exemplary embodiments of flange 29 will be described. In one embodiment, shown in FIG. 6, flange is constructed from additional struts 60 that extend from each of adjacent helical portions 24, 26 into the space between the helical portions. Struts 60 form a plurality of openings 61 that are generally irregularly shaped. However, it will be appreciated that struts 60 may be configured so that openings 61 have any desired shape. As shown in FIG. 7, openings 61 may be enlarged by removing struts 60. FIGS. 8-15 illustrate various other possible configurations of flange 29. In some embodiments, such as those shown in FIGS. 8 and 15, the flange may include a wavy edge. In others, such as those shown in FIGS. 9-14, the flange may include a smooth edge. It should be appreciated, upon inspection of the exemplary embodiments illustrated in FIGS. 6-15 that any shaped cells may be utilized to form flanges with desired characteristics.

The number of and configuration of struts may be tailored as desired to provide various characteristics. For example, including struts 60 that are parallel to the longitudinal axis of the vascular prosthesis may increase longitudinal rigidity and the strength of helical portions 24, 26 near flanges. Additionally, including struts 60 oriented circumferentially about vascular prosthesis may increase radial stiffness of apex 28 of the vascular prosthesis. The flexibility is tailored to improve radial force applied by and/or fatigue strength of the prosthesis or to aid deployment. Additionally, the strut configuration throughout helical portions 24, 26 may also be tailored to provide such characteristics as will be discussed in greater detail below.

Figure 16A:
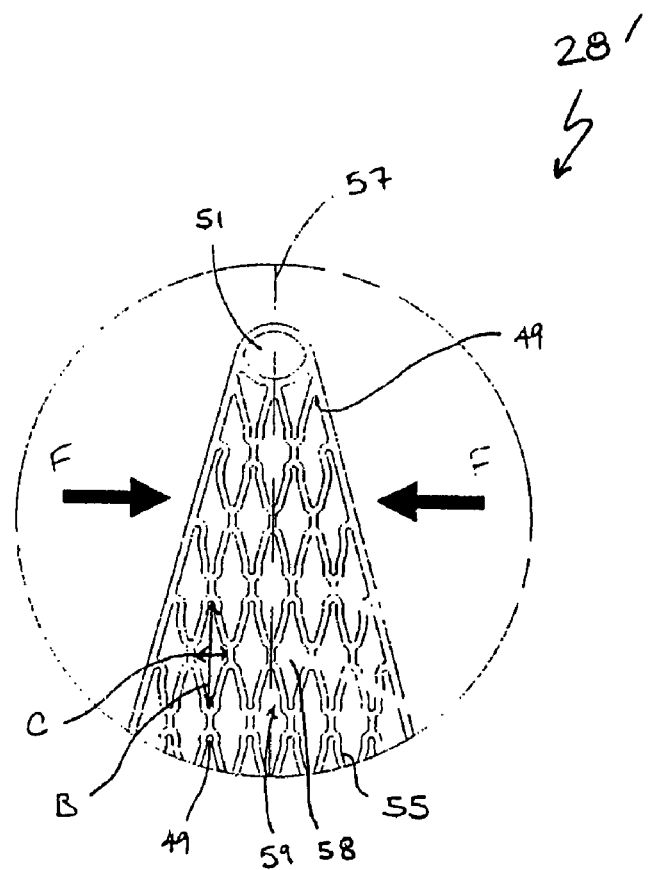
FIGS. 16A and 16B are side views of an apex portion of a vascular prosthesis according to the present invention.
Figure 16B:
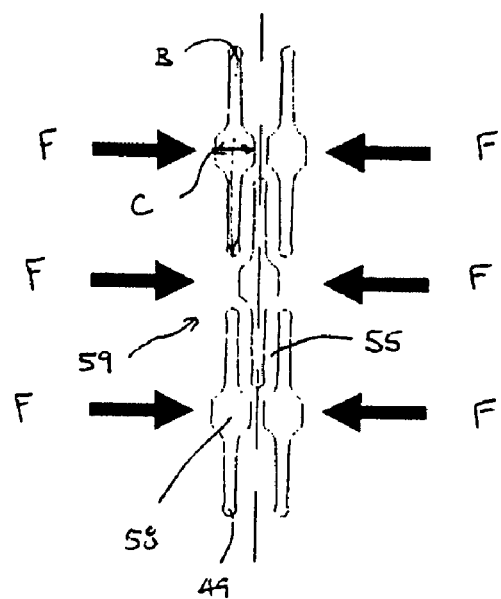

Referring to FIGS. 16A and 16B, an alternative strut configuration for the apices of the vascular prosthesis is described. Apex 28' is constructed with struts 55 that form plurality of cells 59 defining elongate openings 58. Elongate openings 58 allow cells 59 to be compressed in response to longitudinal loads (shown by arrows F) placed on vascular prosthesis 20.

In addition, tip aperture 51, or eyelet, is included in apex 28'. Apertures 51 are provided so that apex 28' may be easily coupled to a delivery device, as will be described in greater detail below. As shown, aperture 51 is generally elliptical, but it should be appreciated that the shape of aperture 51 will generally correspond to the structure of the intended delivery device.

Elongate openings 58 each generally have major axis B corresponding to the longest distance across opening 58 and minor axis C corresponding to the shortest distance across opening 58. Referring to FIG. 16B, a portion of apex 28' of FIG. 16A is shown with cells 59 compressed under the influence of longitudinal force F. Elongate openings 58 are oriented so that major axis B of each opening 58 is parallel with center line 57 of apex 28' and minor axis C of each opening 58 is perpendicular to center line 57. During compression minor axis C is reduced while major axis B remains generally unchanged. As a result, the longitudinal load may be dampened by compression of the mesh structure of vascular prosthesis 20.

Elongate openings 58 preferably are shaped to reduce stress concentration. In the present embodiment, elongate openings 58 are generally diamond-shaped with rounded corners 49 at the junctions of adjacent struts 55. It should be appreciated that elongate openings may be any elongate shape. The size, shape and orientation of cells 59 on either side of center line 57 are shown generally identical. With such a configuration, dampening occurs equally from both sides of center line 57 when a longitudinal load is applied. However, it should be appreciated that the dampening characteristics of vascular prosthesis 20 may be tailored by including cells having different size, shape and/or orientation on either or both sides of center line 57. Furthermore, it should be appreciated that the apices included throughout vascular prosthesis 20 need not be identical and may be configured to provide differing dampening characteristics throughout vascular prosthesis 20.

Figure 17:
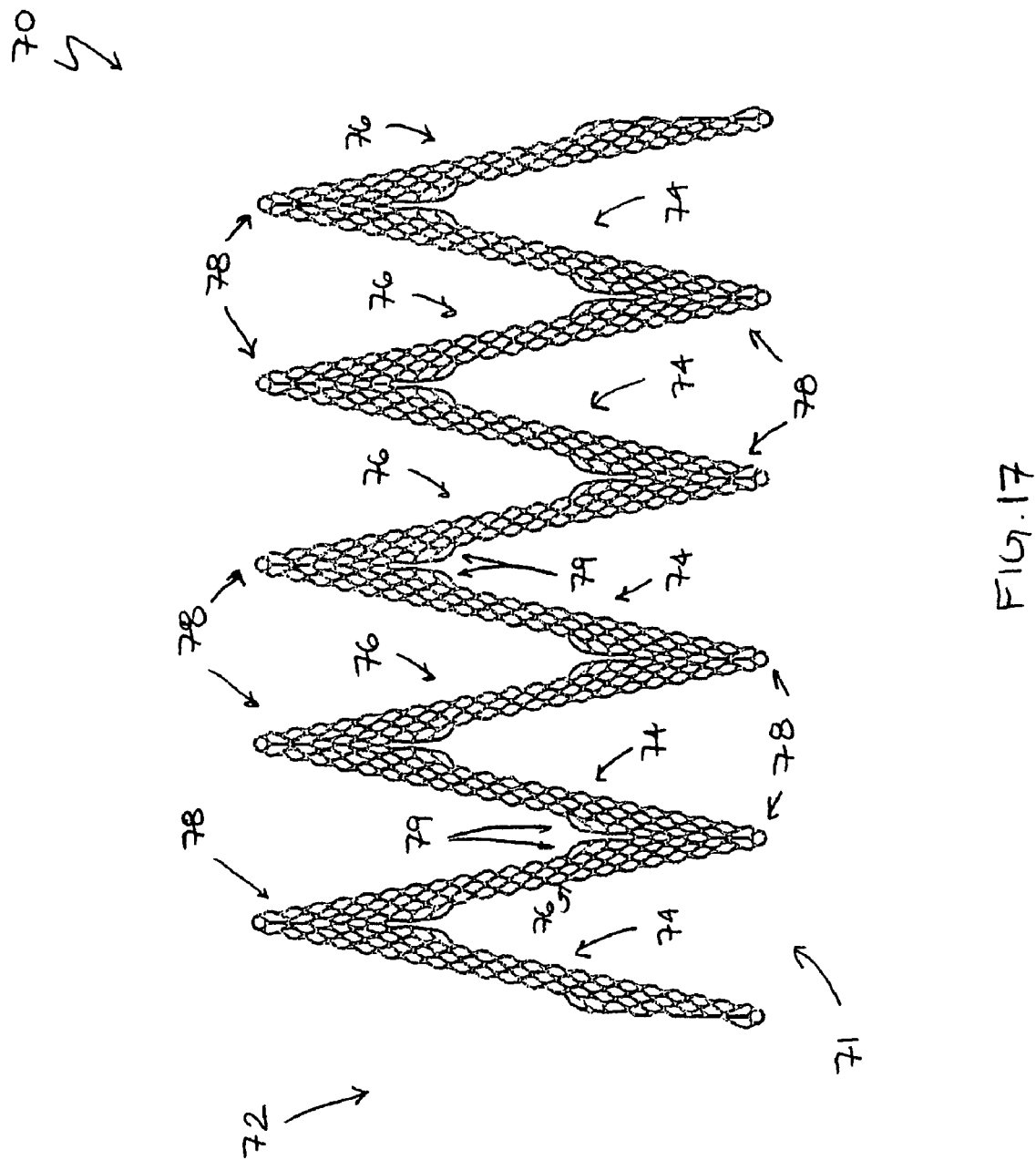
FIG. 17 is a side view of another embodiment of a vascular prosthesis of the present invention.

Referring to FIG. 17, another embodiment of vascular prosthesis 70 will be described. Vascular prosthesis 70 generally includes alternating helical section 71. Alternating helical section 71 includes a plurality of helical portions 74, 76 that have alternating directions of rotation and are joined by apices 78. The edges of helical portions 74, 76 are wavy, which may be provided so that a relative sliding of the portions of alternating helical section 81 may provide a ratchet effect so that the overlapping portions may be incrementally and temporarily interlocked during deployment. A flange 79 is included on each helical portion adjacent to apices 78. As described previously, flanges 79 are widened portions of helical portions 74, 76 that are used to maintain a desired amount of metal coverage and may be used to retain apices in their respective radial position throughout a portion of use of vascular prosthesis 70. For example, when vascular prosthesis 70 is in a contracted state, apices 78 are either located radially outward or inward of corresponding flanges 79. Flanges 79 are configured so that when vascular prosthesis is transitioned to a deployed state, each apex 78 remains in the same radial relationship with corresponding flange 79. It will be appreciated that although vascular prosthesis 70 is illustrated having flanges 79 with configurations generally corresponding to those of FIG. 6, any flange configuration may be incorporated.

Figure 18:
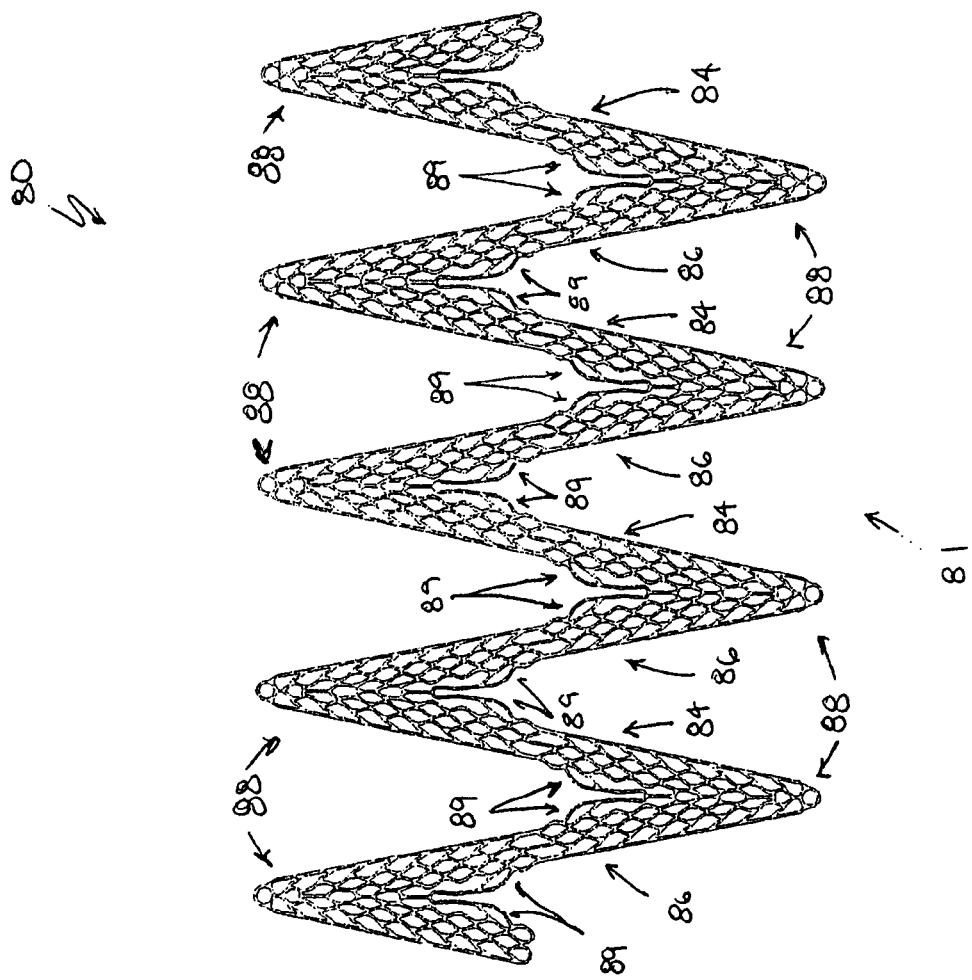
FIG. 18 is a side view of another embodiment of a vascular prosthesis of the present invention.

Referring to FIG. 18, another embodiment of vascular prosthesis 80 will be described. Vascular prosthesis 80 generally includes alternating helical section 81. Alternating helical section 81 includes a plurality of helical portions 84, 86 that have alternating directions of rotation and are joined by apices 88. In addition, the edges of helical portions 84, 86 are straight rather than wavy, which may be provided so that relative sliding of portions of alternating helical section 81 may be simplified during deployment. Moreover, the tip or tail portion of each of the helical portions on the proximal and distal ends of alternating helical portion 81 have been truncated. A flange 89 also is included on each helical portion adjacent to apices 88. As described previously, flanges 89 are widened portions of helical portions 84, 86 that retain apices in their respective radial position throughout use of vascular prosthesis 80. It will be appreciated that although vascular prosthesis 80 is illustrated having flanges 89 with configurations generally corresponding to those of FIG. 6, any flange configuration may be incorporated.

Figure 19:
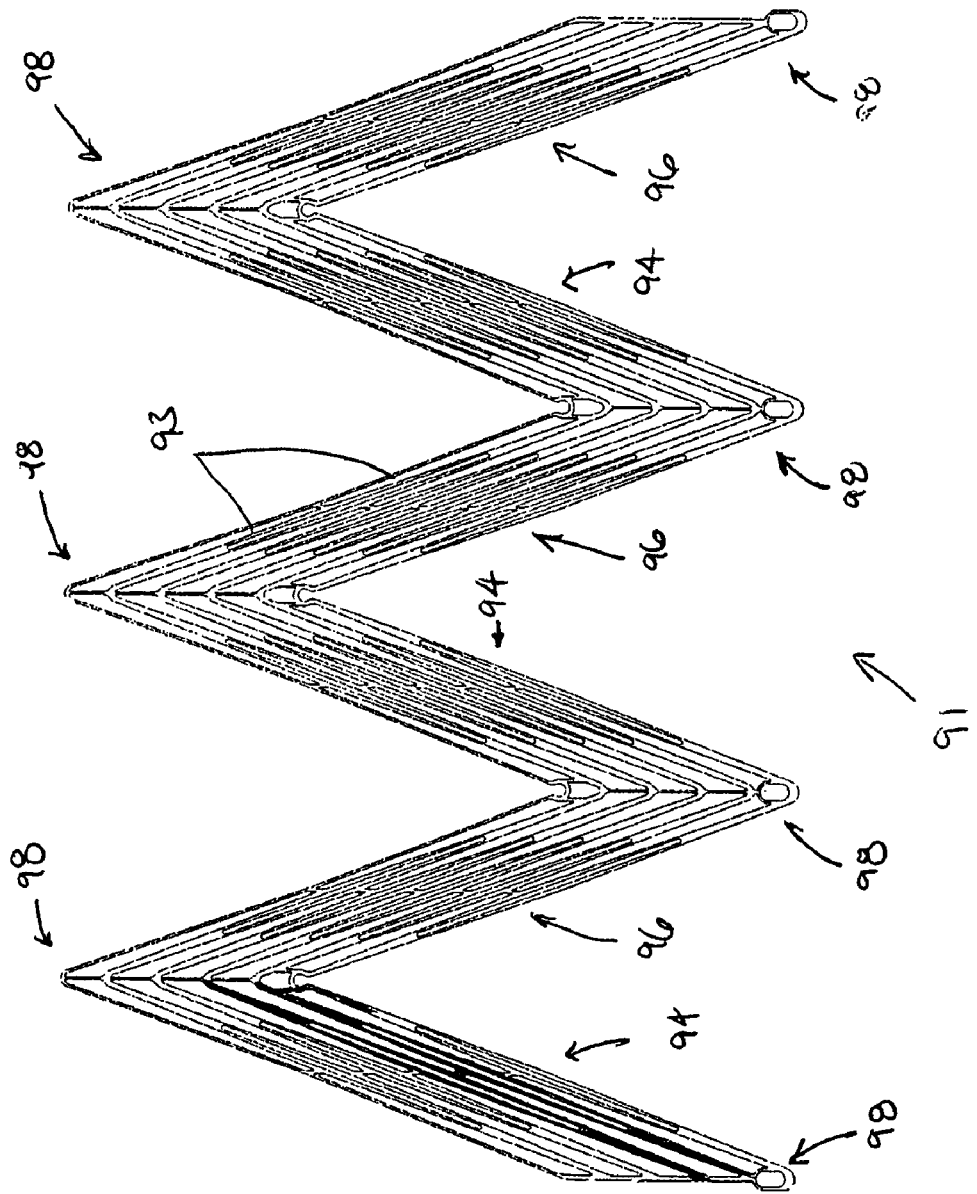
FIG. 19 is a side view of another embodiment of a vascular prosthesis of the present invention.

In yet another embodiment, shown in FIG. 19, alternating helical section 91 includes helical portions 94, 96 that are formed with elongated openings 93 that extend substantially the entire length of the respective helical portion. The struts that form openings 93 have a greater thickness adjacent apices 98 than the thickness at locations spaced between apices 98. Such graduated thickness may be used to control radial strength of the stent or so that the radial forces exerted by vascular prosthesis during expansion and compression are uniform at different locations around the circumference of the vascular prosthesis. For example, the radial force exerted by apices 98 may be altered so that it is approximately equal to the force exerted by the remainder of each helical portion of alternating helical section 91 by altering the thickness of the struts. As shown, the struts near apex 98 have a greater thickness to reduce the flexibility of the vascular prosthesis near apex 98.

As will be apparent to one skilled in the art, the configuration of the alternating helical sections depicted herein is merely for illustrative purposes. Any combination of covered portions and openings of any shape and size may be provided along the helical portions, as desired to provide a desired amount of metal coverage. Alternatively, one or more helical portions may be completely solid, such that the openings are omitted entirely from that portion.

As will be apparent to those skilled in the art, a combination of solid regions and openings may be provided along the length of the alternating helical section, for example, to selectively increase surface area and drug delivery capabilities along the alternating helical section, or to influence flow dynamics within a vessel.

It will be appreciated that different drug delivery modalities may be used in conjunction with the vascular prosthesis of the present invention. For example, vascular prosthesis may include one or more dimples and/or through holes that may have a therapeutic agent disposed therein. As a further alternative, a therapeutic agent may be incorporated into the any of the openings previously described above. As a still further alternative, a therapeutic agent may be disposed in the matrix of a bioabsorbable polymer coated on any portion of the vascular prosthesis, and the drug may be gradually released into a localized region of a vessel wall.

One or more of the helical portions also may be selectively coated with an elastomeric polymer, such as polyurethane. The elastomeric polymer may partially or fully cover the selected portions. For example, the elastomeric polymer may be disposed on a portion of the circumference of the alternating helical section, e.g., to reduce blood flow into a sac of the aneurysm. As a further alternative, the entire alternating helical section may be covered so that the device may be used as a stent graft. In such an embodiment, ePTFE and DACRON are examples of materials that may be used to cover the alternating helical section. It should also be appreciated that covering material may be included within the openings of the mesh structure so that it fills the openings without increasing the overall diameter of the struts. Additionally, a therapeutic agent may be disposed on the elastomeric polymer to increase the working surface area of the alternating helical section. Alternatively, the therapeutic agent may be disposed directly on the alternating helical section, either with or without the use of a elastomeric polymer.

The therapeutic agent may include, for example, antiplatelet drugs, anticoagulant drugs, antiproliferative drugs, agents used for purposes of providing gene therapy to a target region, or any other agent, and may be tailored for a particular application. Radiopaque markers (not shown) also may be selectively disposed on any portion of vascular prosthesis including in the vicinity of the therapeutic agents to facilitate alignment of the therapeutic agents with a target site of a vessel wall. Advantageously, higher doses of such agents may be provided using the vascular prosthesis of the present invention, relative to previously known coils or stents having interconnected struts, due to the increased surface area associated with the alternating helical section.

In operation, the overlap of portions of the alternating helical section when it is in the contracted state and the number of helical portions, causes alternating helical section 101 to deploy in a unique sequence, as will be described in greater detail below with reference to FIGS. 21A-21D. Advantageously, the order of deployment of the portions of alternating helical section 101 alleviates drawbacks associated with the prior art such as the tendency of the turns of the helical section to jump or shift during deployment and also results in the location of deployment being more easily controlled. Another benefit is that deployment of discrete segments may be more easily controlled. Additionally, the alternating helical section may be balloon expandable. In particular, the structure allows a user to post dilate discrete sections with a balloon. For example, a user may expand a selected portion of the device adjacent a specific apex.

Figure 20:
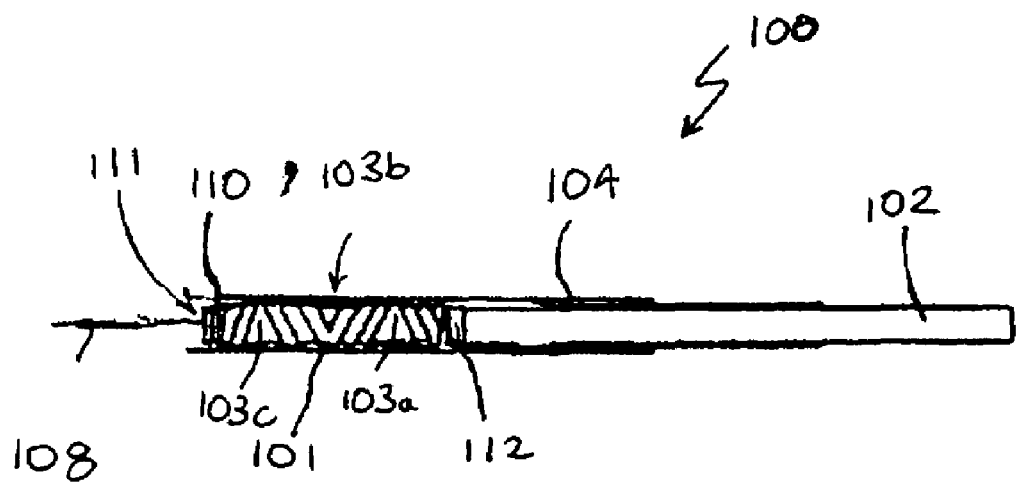
FIG. 20 is a cross-sectional view of a delivery system suitable for use in delivering the vascular prosthesis of FIG. 3.

In FIG. 20, a delivery system 100 suitable for use in delivering a vascular prosthesis of the present invention is described. Delivery system 100 comprises catheter body 102, outer sheath 104, and a lumen dimensioned for the passage of guidewire 108. Catheter body 102 preferably includes distal marker 111 and stop 110 located adjacent the distal end of alternating helical section 101 and proximal stop 112 located adjacent the proximal end of alternating helical section 101.

Distal stop 110 may comprise a raised ledge on catheter body 102 so that the distal end of alternating helical section 101 bears on the ledge to prevent relative movement between alternating helical section 101 and catheter body 102 in the distal direction. Alternatively, distal stop 110 may comprise a plurality of raised pins or knobs that prevent relative motion between alternating helical section 101 and catheter body 102 parallel to the longitudinal axis. Proximal stop 112 also may comprise a raised ledge, pins or knobs on catheter body 102, and both distal and proximal stops 110 and 112 may be radiopaque, so as to be visible under a fluoroscope and provide a radiopaque marker. It should be appreciated that any portion of the delivery device or vascular prosthesis may include one or more radiopaque markers.

Vascular prosthesis 109 is collapsed onto catheter body 102 by winding alternating helical section 101 around catheter body 102. In order to wind alternating helical section 101 on catheter body 102, apices 103a and 103c may be temporarily coupled to catheter body 102 and the remainder of alternating helical section 101 is wound around catheter body 102 until it is collapsed as shown in FIG. 20.

After alternating helical section 101 is wound on catheter body 102, outer sheath 104 is advanced distally over catheter body 102 to capture alternating helical section 101 between catheter body 102 and outer sheath 104.

Figure 21A:
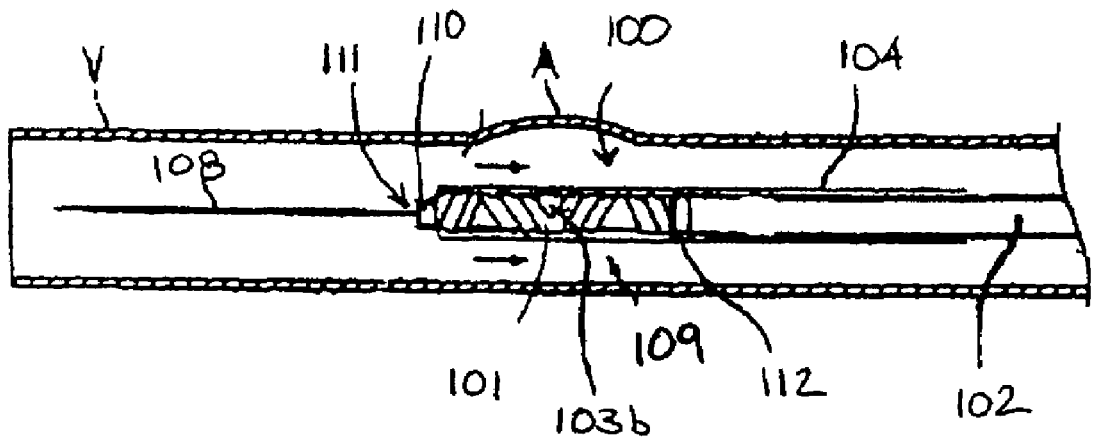
FIGS. 21A-21D are side sectional views illustrating use of the vascular prosthesis in the treatment of an aneurysm.

Referring to FIG. 21A, in operation, guidewire 108 is percutaneously and transluminally advanced through a patient's vasculature, using techniques that are known in the art. Guidewire 108 is advanced until a distal end of guidewire 68 is positioned distal of aneurysm A, which is situated in vessel V. Delivery system 100, having vascular prosthesis 109 contracted therein, then is advanced over guidewire 108 through the central lumen of catheter body 102. Delivery system 100 preferably is advanced under fluoroscopic guidance until distal marker 111 is situated distally to aneurysm A and alternating helical section 101 and apex 103b are situated adjacent to the aneurysm.

Once alternating helical section 101 is located adjacent to aneurysm A, outer sheath 104 is retracted proximally to cause alternating helical sections to deploy until outer sheath 104 is retracted to proximal stop 112.

Figure 21B:
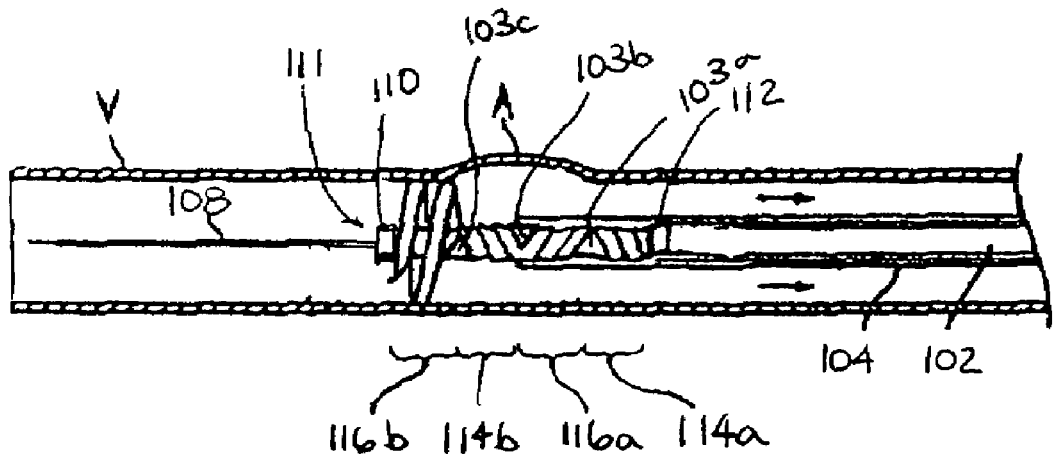
Figure 21C:
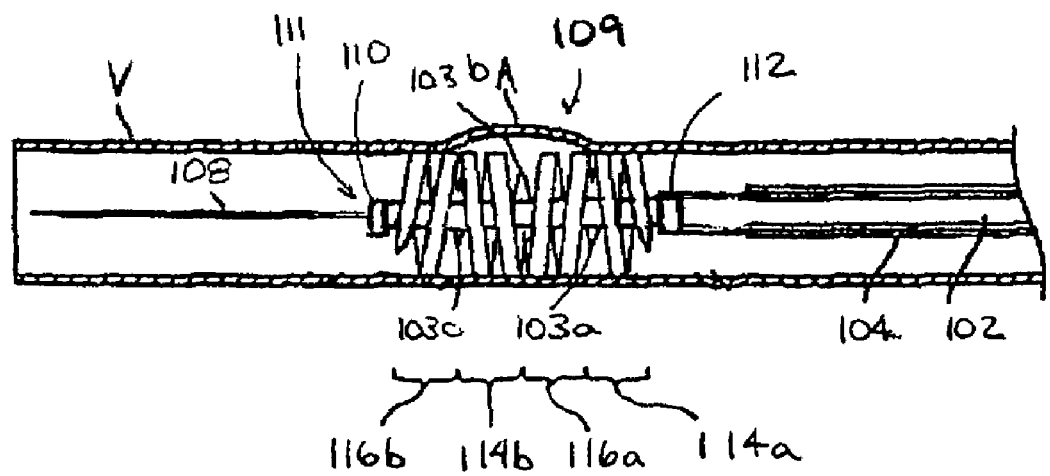

Referring to FIGS. 21B and 21C, after the distal end of alternating helical section 101 is secured distal of aneurysm A, outer sheath 104 is further retracted proximally to allow alternating helical section 101 to continue to expand and deploy to its predetermined deployed shape. During proximal retraction of outer sheath 104, the stent rotates within the artery, or may be manually rotated through rotation of the delivery system, to enable alternating helical section 101 to unwind. Because central portions of the alternating helical section are over-wrapped, rotation of catheter body 102 is not required for the alternating helical section to expand.

As outer sheath 104 is further retracted, the turns of alternating helical section 101 unwinds and engages and conforms to an inner wall of vessel V in a controlled manner. Helical portion 116b expands as outer sheath 104 is moved proximal of the distal end of alternating helical section 101. Helical portion 116b is not able to expand until the distal end of outer sheath 104 is moved proximal of apex 103b because alternating helical section 101 is wound so that apex 103b is located radially outward (i.e., outer-wrapped) and overlaps the adjacent helical portions. After the distal end of outer sheath 104 is moved proximal of apex 103b, helical portions 114b and 116a are allowed to expand. For example, inner-wrapped apices, such as apices 103a and 103c, are constrained by the adjacent helical portions 114 and 116 and as a result those apices remain constrained until sufficient exposure of the stent occurs to release the helical portions, thereby creating a controlled release of the stent. Finally, after sheath 104 is moved proximal of the proximal end of alternating helical section 101, helical portion 114a is able to expand, as illustrated in FIG. 21C.

Proximal movement of outer sheath 104 may be halted once the distal edge of outer sheath 104 is substantially aligned with proximal stop 112 to allow alternating helical section 101 to expand. It will be appreciated that because of the sequence of deployment of alternating helical section 101, the location of the deployed alternating helical section 101 may be easily controlled and the problems encountered in previous systems (e.g., stent jumping) may be avoided.

Figure 21D:
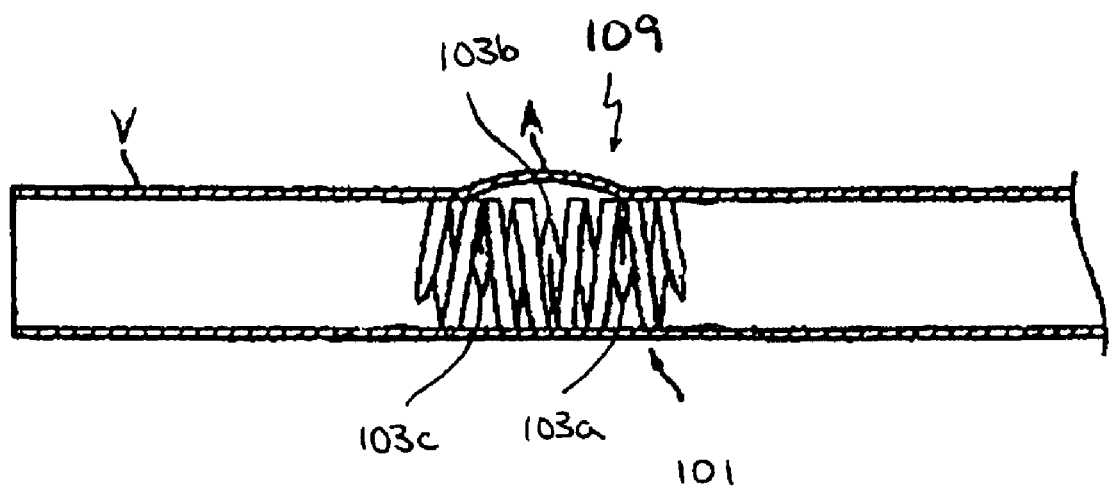

When vascular prosthesis 109 is fully deployed, delivery system 100 is proximally retracted over guidewire 108 and withdrawn from the patient's vessel, and guidewire 108 is removed. After removal of delivery system 100 and guidewire 108, vascular prosthesis 109 remains deployed, as shown in FIG. 21D.

In the present invention, the partial overlap of portions of alternating helical section 101 reduce the surface area that is available to frictionally engage an inner surface of outer sheath 104. Furthermore, the sequence of deployment of the alternating helices included in alternating helical section 101 also assures that the prosthesis remains properly located during deployment. Advantageously, the helical portions of the alternating helical section will be accurately deployed within vessel V, with substantially no proximal or distal shifting or foreshortening of the prosthesis with respect to the vessel as the outer sheath of the delivery device is retracted.

It should be appreciated that the furthest proximal and the furthest distal helical portions may be configured so that the proximal and distal tips of the alternating helical section are either inner-wrapped or outer-wrapped as desired. As shown in FIGS. 21A-D both tips may be outer-wrapped. As a further alternative, one tip may be inner-wrapped. It will be appreciated that inner-wrapped portions of the alternating helical section generally require expansion of complimentary portions of the alternating helical section before the entire prosthesis is capable of expansion.

Figure 22:
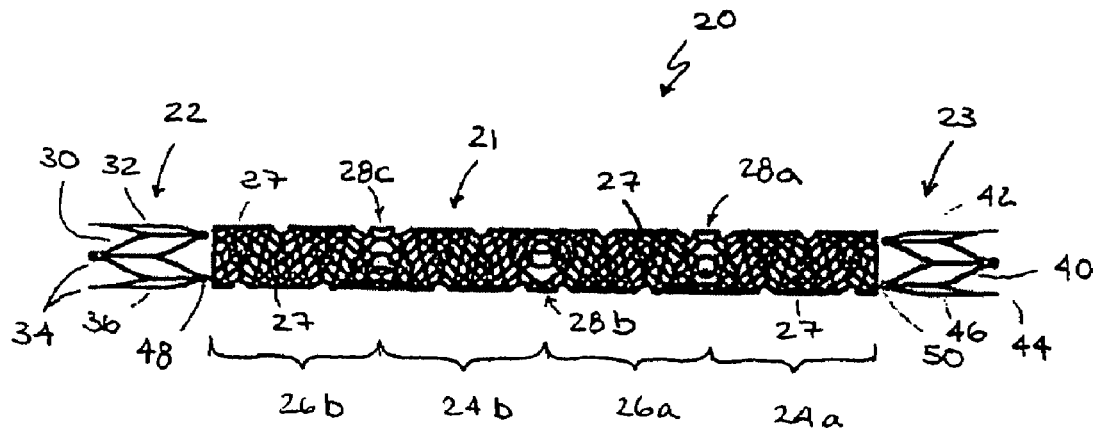
FIG. 22 is a side view of a vascular prosthesis of the present invention that includes distal and proximal anchors.
Figure 23:
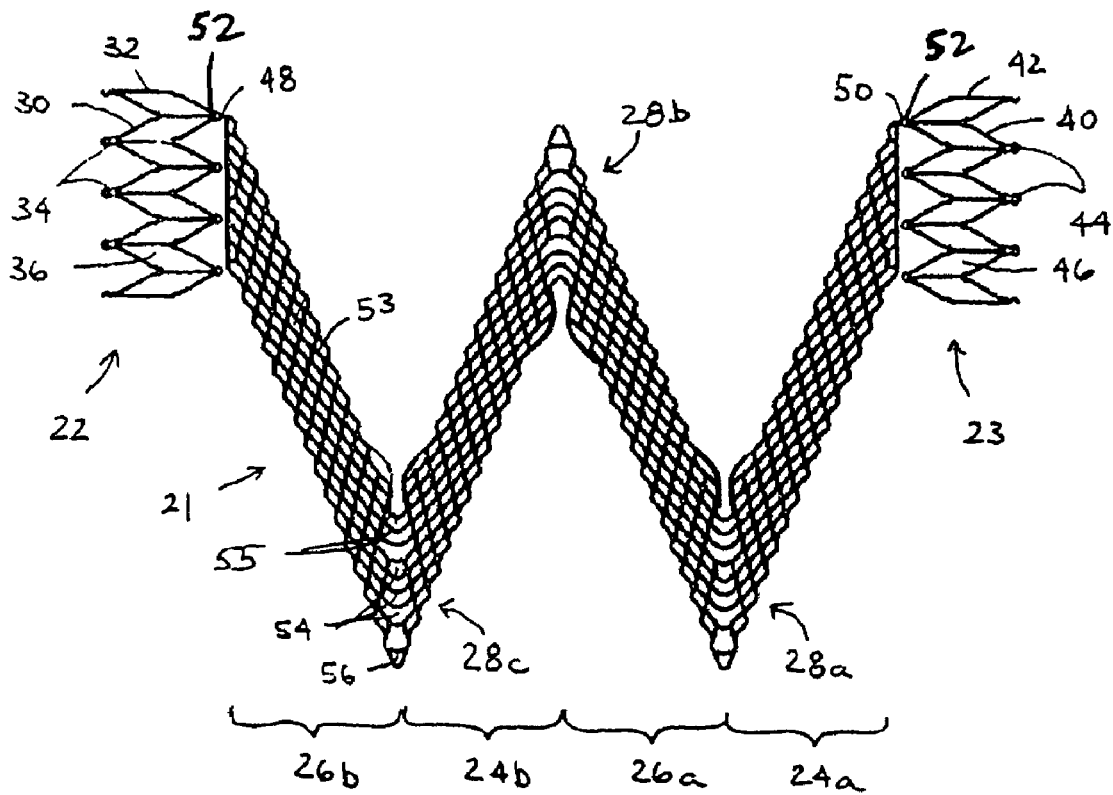
FIG. 23 is a schematic representation of the vascular prosthesis of FIG. 22 shown in a flattened configuration.

Referring to FIGS. 22 and 23, another embodiment of vascular prosthesis 20 is shown, which includes optional distal and proximal anchor sections 22, 23. Distal anchor section 22 preferably is a tubular mesh structure that is coupled to a distal end of alternating helical section 21. In particular, distal anchor section 22 includes a pair of concentrically aligned zig-zag rings 30 that are spaced from one another and coupled by struts 32. Struts 32 extend between corresponding apices 34 of rings 30 and are oriented parallel to a longitudinal axis of vascular prosthesis 20. Apices 34 may comprise one or more radiopaque markers 33 such as a radiopaque marker band or coating. As a result, rings 30 and struts 32 combine to define a plurality of openings 36 shaped as parallelograms, thereby forming a tubular mesh. The tubular mesh preferably is formed by laser cutting a solid tube.

Distal anchor section 22 preferably is formed from a solid tubular member comprising a shape memory material, such as nickel-titanium alloy, which is laser cut, using techniques that are known in the art, to a desired deployed configuration. Preferably, distal anchor section 22 is cut from the tube so that rings 30 and struts 32 are formed as a single monolithic body. However, it should be appreciated that distal anchor section 22 may be constructed from separate rings 30 and struts that are mechanically coupled in a secondary operation, such as by welding, soldering or employing a mechanical fastener, such as a rivet. An appropriate heat treatment then may be applied so that distal anchor section 22 may be configured to self-deploy radially outward from a contracted, delivery configuration to a deployed configuration in conjunction with alternating helical section 21, described above. Alternatively, distal anchor section 22 may be configured to be balloon expandable.

Proximal anchor section 23 also preferably has a tubular mesh construction. Proximal anchor section 23 includes pair of concentrically aligned zig-zag rings 40 that are spaced from one another and coupled by struts 42. Struts 42 extend between corresponding apices 44. Apices 44 may comprise one or more radiopaque markers 43 such as a radiopaque marker, band or coating. Rings 40 are oriented parallel to longitudinal axis X of vascular prosthesis 20. Rings 40 and struts 42 combine to define a plurality of openings 46 shaped as parallelograms. Similar to distal anchor section 22, the tubular mesh structure of proximal anchor section 23 preferably is formed by laser cutting a solid tube. Proximal anchor section 23 may be constructed in the same manner described above with respect to distal anchor section 22. Alternatively, proximal anchor section 23 also may be constructed to be balloon expandable.

Moreover, distal anchor section 22 and proximal anchor section 23 may have different constructions. Although distal anchor section 22 and proximal anchor section 23 as described above are identical, they alternatively may have different zig-zag or cell structures or deployment modes (e.g., self-expanding at the distal end and balloon expandable at the proximal end). For example, anchor sections 22, 23 may be constructed as a single zig-zag ring. As a further alternative, anchor sections 22, 23 may be configured so that openings 36, 46 have shapes other than parallelograms, e.g., openings 36, 46 may be shaped as diamonds or any other polygonal shape, circles or ellipses. Furthermore, although anchor sections 22, 23 are illustrated as including struts 32, 42 extending between each set of corresponding apices, struts 32, 42 may extend between fewer sets of corresponding apices. For example, struts may extend between relatively few apices. In addition, the distance between the zig-zag rings of anchor sections 22, 23 may also be selected to provide an anchor section of any desired length.

Furthermore, the outer edges of anchor sections 22, 23 may be biased so that the proximal-most edge of anchor section 23 and the distal-most edge of anchor section 22 expand further radially outward than with respect to longitudinal axis X than the remainder of the anchor section. This configuration may be useful to increase radial outward force upon a patient's vessel and thus improve anchoring of vascular prosthesis 20 within the vessel. Such a biased configuration may be established by heat-treating a shape memory material using techniques that are known in the art.

Distal anchor section 22 is coupled to the distal end of alternating helical section 21 at junction 48. Similarly, proximal anchor section 23 is coupled to the proximal end of alternating helical section 21 at junction 50. Preferably, junctions 48, 50 are formed from a strut of alternating helical section 21 that extends from that section and is coupled to a portion of the adjacent zig-zag rings 30, 40 of the respective anchor section 22, 23.

Junctions 48, 50 may comprise one or more radiopaque markers 52 such as a radiopaque marker band or coating. Radiopaque marker 52 facilitates positioning of junctions 48, 50 at a desired longitudinal position within a patient's vessel, and further facilitates alignment of vascular prosthesis 20 at a desired axial orientation within the vessel. For example, radiopaque markers 52 may be used to orient alternating helical section 21 so that a desired lateral surface of alternating helical section 21 deploys to overlay the diseased vessel segment.

It will be apparent to those skilled in the art that junctions 48, 50 may comprise other strut arrangements to connect distal anchor section 22 and proximal anchor section 23 to alternating helical section 21. For example, more than one strut may extend from alternating helical section 21 to a respective anchor 22, 23.

In one preferred embodiment, alternating helical section 21, distal anchor section 22 and proximal anchor section 23 are integrally formed as a single monolithic body, such as by laser cutting all three components from a single tube. In such a construction of vascular prosthesis 20, the struts extending from alternating helical section 21 that form junctions 48, 50 also may form struts 32, 42 of the respective anchor section 22, 23. Alternatively, anchor sections 22, 23 may be manufactured separately from alternating helical section 21 and mechanically coupled in a subsequent process, such as by soldering, welding, installing mechanical fasteners (e.g., rivets) or other means, as will be apparent to one skilled in the art.

Figure 24:
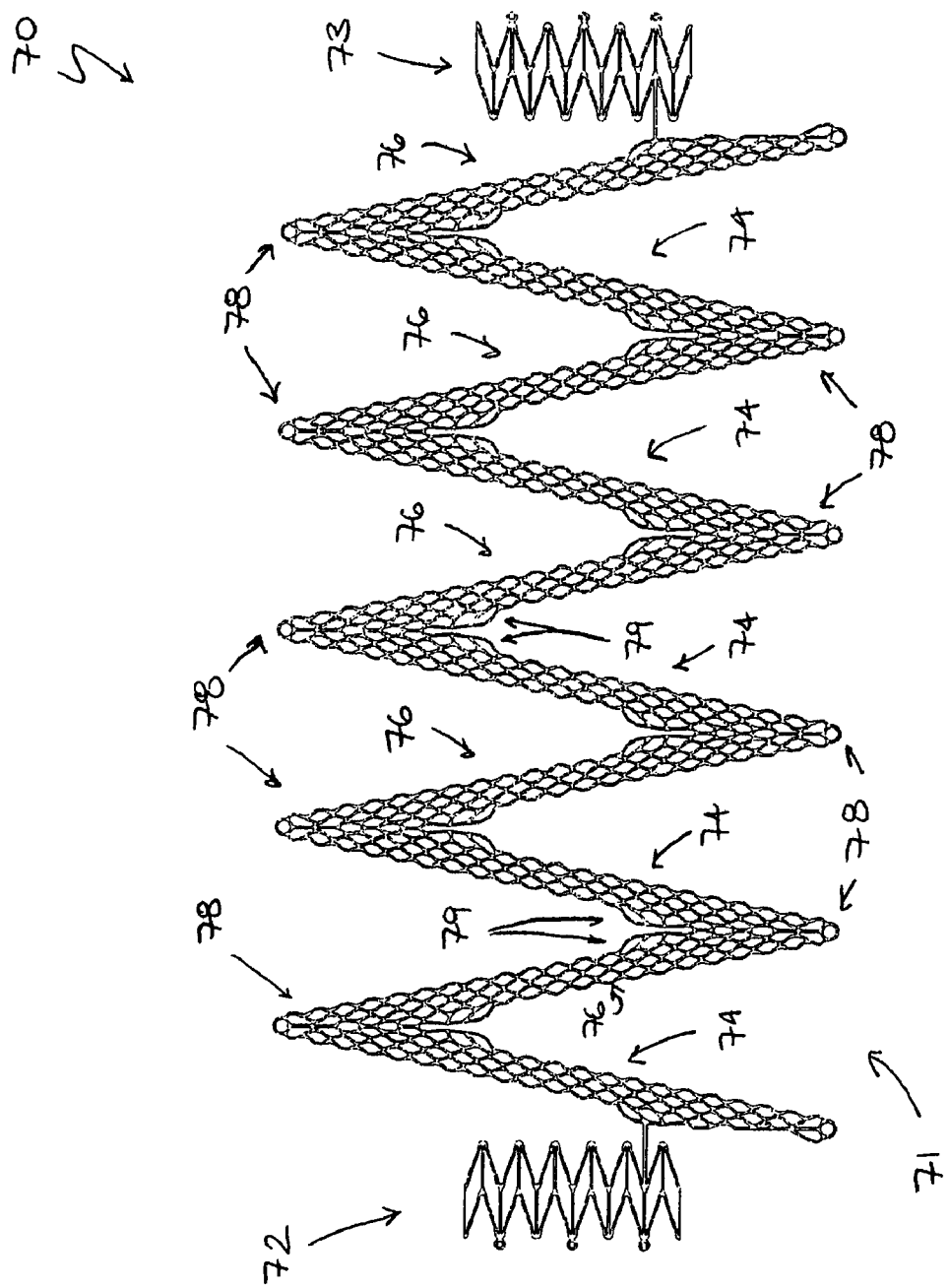
FIG. 24 is a side view of another embodiment of a vascular prosthesis of the present invention.

Referring to FIG. 24, another embodiment of the vascular prosthesis will be described. The present embodiment illustrates a version of vascular prosthesis 70, described above that includes distal anchor 72 and proximal anchor 73. Distal and proximal anchors 72, 73 are similar in construction to those described with respect to FIGS. 22 and 23. Alternating helical section 71 is similar in construction to that described with respect to FIG. 17 and will not be further described.

Figure 25:
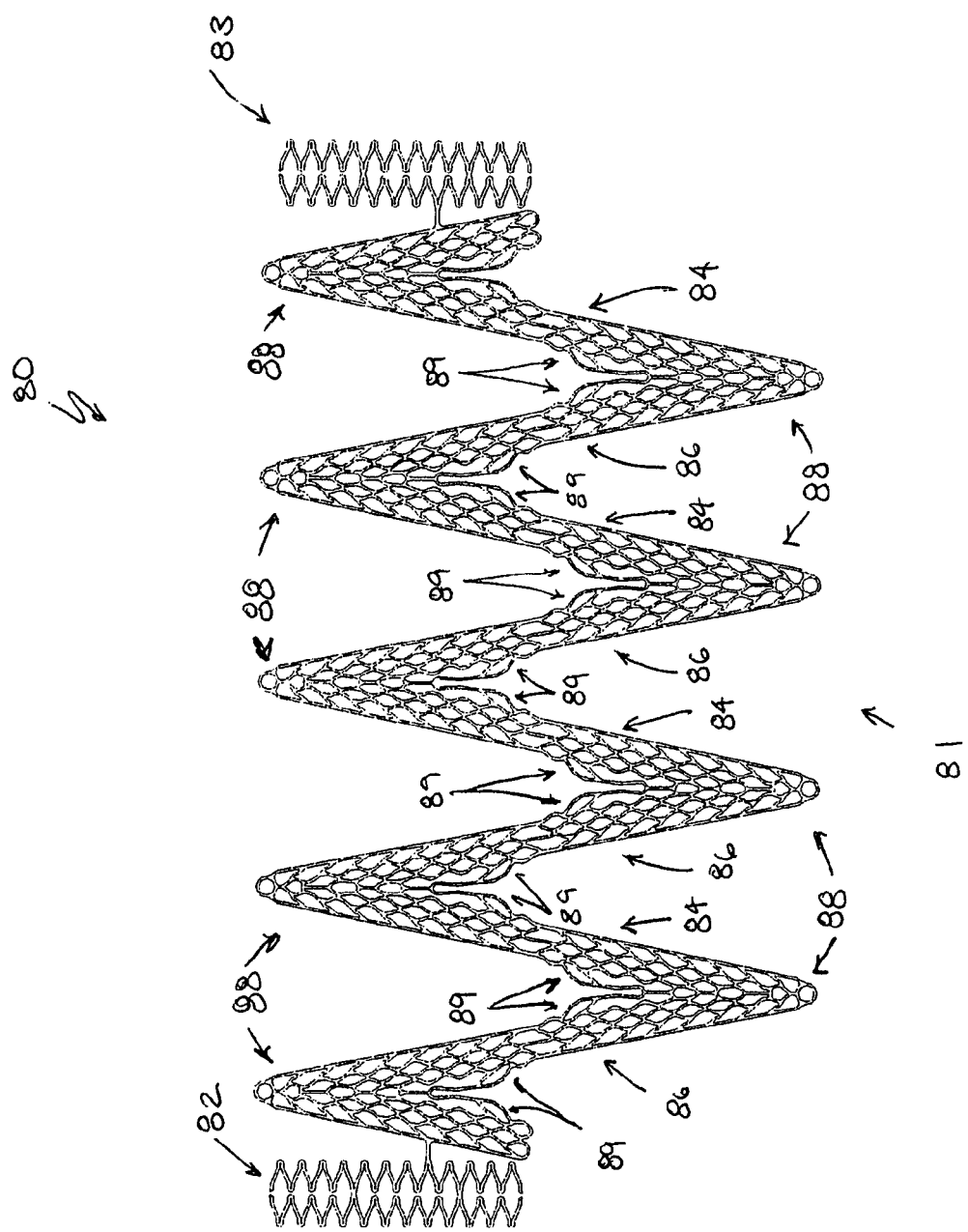
FIG. 25 is a side view of another embodiment of a vascular prosthesis of the present invention.

Referring to FIG. 25, another embodiment of the vascular prosthesis will be described. The present embodiment illustrates a version of vascular prosthesis 80, described above, that includes distal anchor 82 and proximal anchor 83. Distal and proximal anchors 82, 83 are similar in construction to those described with respect to FIGS. 22 and 23 but include zig-zag rings that are slightly offset to define diamond-shaped openings and fewer struts between the rings are employed. Alternating helical section 81 is similar in construction to that described with respect to FIG. 18 and will not be further described.

A further advantage over the above-mentioned publications is that the configuration of the alternating helical section provides dampening characteristics for longitudinal, torsional and buckling forces applied to the vascular prosthesis.

Although a method of treating diseased vessels has been described, it will be apparent from the method described herein that the vascular prosthesis may be used in a variety of procedures. For example, vascular prosthesis also may be used in general stenting procedures, for example, to maintain patency in a vessel after a carotid angioplasty procedure, or may be used as an intravascular drug delivery device, or may be used in other applications apparent to those skilled in the art.

In accordance with another aspect of the present invention, the vascular prosthesis of the present invention is configured to be flexible enough to substantially conform to the shape of vessel V without causing the vessel to remodel. In particular, the alternating direction of rotation of the helical portions of the alternating helical section allow for increased flexibility of the prosthesis.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A vascular prosthesis for implantation in a body vessel having a vessel wall, the vascular prosthesis placeable in radially contracted and expanded states, the vascular prosthesis comprising:
    an alternating helical section comprising first and second helical portions;
    the first helical portion having a direction of rotation about a longitudinal axis of the prosthesis opposite to that of the second helical portion;
    the first and second helical portions having adjacent ends joined directly to one another to define a first apex;
    each of the first and second helical portions comprising a widened flange portion adjacent to the first apex;
    the widened flange portions extending into a space between the first and second helical portions;
    the widened flange portions separated from one another by a gap; and
    the widened flange portions being configured to overlap a portion of the apex during at least a portion of a treatment range between the radially contracted and expanded states.

2. The vascular prosthesis of claim 1, wherein the alternating helical section includes an even number of helical portions having a first direction of rotation and an even number of helical portions having a second direction of rotation, wherein the helical portions define an odd number of apices.

3. The vascular prosthesis of claim 1, wherein the alternating helical section includes an even number of helical portions having a first direction of rotation and an odd number of helical portions having a second direction of rotation, wherein the helical portions define an even number of apices.

4. The vascular prosthesis of claim 1, wherein the flanges have straight edges.

5. The vascular prosthesis of claim 1, wherein the flanges have zig-zagged edges.

6. The vascular prosthesis of claim 1, wherein at least one helical portion is a helical mesh.

7. The vascular prosthesis of claim 6, wherein the helical mesh defines a plurality of elongate apertures.

8. The vascular prosthesis of claim 7, wherein a plurality of the elongate apertures extend from a first apex to a second apex.

9. The vascular prosthesis of claim 1, further comprising a therapeutic agent disposed on or in a portion of the alternating helical section.

10. The vascular prosthesis of claim 1, further comprising a polymer disposed on or in a portion of the alternating helical section.

11. The vascular prosthesis of claim 10, wherein the polymer is configured to elute a therapeutic agent.

12. The vascular prosthesis of claim 10, wherein the polymer is disposed on the entire alternating helical section.

13. The vascular prosthesis of claim 1, wherein the alternating helical section comprises a shape memory material.

14. The vascular prosthesis of claim 13, wherein the shape memory material is a nickel titanium alloy.

15. The vascular prosthesis of claim 1, further comprising a radially expanding anchor section joined to a first end of the alternating helical section.

16. The vascular prosthesis of claim 15, further comprising a second radially expanding anchor section joined to a second end of the alternating helical section.

17. The vascular prosthesis of claim 16, wherein the alternating helical section, the first anchor section and the second anchor section each are capable of assuming a contracted state suitable for transluminal insertion into the body vessel and a deployed state wherein the helical section, first anchor section and second anchor section are configured to engage the vessel wall.

18. The vascular prosthesis of claim 15, wherein the alternating helical section and the anchor section are separately formed and then coupled together.

19. The vascular prosthesis of claim 15, wherein the alternating helical section and the anchor section are integrally formed.

20. The vascular prosthesis of claim 1, wherein the first apex has first and second circumferentially separated ends, the widened flange portions located at the first end; and
    the overlapped portion of the apex located at the second end.

* * * * *